US009465030B2

(12) United States Patent
Nakatsura et al.

(10) Patent No.: US 9,465,030 B2
(45) Date of Patent: Oct. 11, 2016

(54) KIT FOR DIAGNOSING MALIGNANT MELANOMA

(71) Applicants: NATIONAL CANCER CENTER, Tokyo (JP); LSIP, LLC, Tokyo (JP)

(72) Inventors: Tetsuya Nakatsura, Kashiwa (JP); Keigo Saito, Kashiwa (JP)

(73) Assignees: NATIONAL CANCER CENTER, Tokyo (JP); LSIP, LLC, Tokyo (JP)

( * ) Notice: Subject to any disclaimer, the term of this patent is extended or adjusted under 35 U.S.C. 154(b) by 0 days.

(21) Appl. No.: 14/408,883

(22) PCT Filed: Jun. 17, 2013

(86) PCT No.: PCT/JP2013/066631

§ 371 (c)(1),
(2) Date: Dec. 17, 2014

(87) PCT Pub. No.: WO2013/191146

PCT Pub. Date: Dec. 27, 2013

(65) Prior Publication Data

US 2015/0198598 A1 Jul. 16, 2015

(30) Foreign Application Priority Data

Jun. 18, 2012 (JP) ................................ 2012-137019

(51) Int. Cl.

| | |
|---|---|
| ***G01N 33/577*** | (2006.01) |
| ***C07K 16/18*** | (2006.01) |
| ***G01N 33/574*** | (2006.01) |
| ***C07K 16/30*** | (2006.01) |
| ***C12N 5/16*** | (2006.01) |
| ***C07K 16/22*** | (2006.01) |

(52) U.S. Cl.

CPC ........... *G01N 33/5743* (2013.01); *C07K 16/18* (2013.01); *C07K 16/22* (2013.01); *C07K 16/303* (2013.01); *C07K 16/3053* (2013.01); *C12N 5/16* (2013.01); *G01N 33/577* (2013.01); *C07K 2319/00* (2013.01); *C12N 2510/02* (2013.01); *G01N 2333/4722* (2013.01); *G01N 2333/4727* (2013.01)

(58) Field of Classification Search

None

See application file for complete search history.

(56) References Cited

U.S. PATENT DOCUMENTS

| | | | |
|---|---|---|---|
| 6,401,754 | B1 | 6/2002 | Winquist et al. |
| 2008/0044818 | A1 | 2/2008 | Nishimura et al. |
| 2009/0111095 | A1 | 4/2009 | Nishimura et al. |

FOREIGN PATENT DOCUMENTS

| | | | |
|---|---|---|---|
| EP | 1813843 | A1 | 8/2007 |
| WO | 2005039380 | A2 | 5/2005 |
| WO | 2006043362 | A1 | 4/2006 |

OTHER PUBLICATIONS

International Search Report dated Jul. 9, 2013 corresponding to PCT/JP2013/066631.
Supplementary Partial European Search Report corresponding to EP-13806194, dated Dec. 22, 2015.
Y. Ikuta, et al., "Highly Sensitive Detection of Melanoma at an Early Stage Based on the Increased Serum Secreted Protein Acidic and Rich in Cysteine and Glypican-3 Levels," Clin Cancer Res 2005; 11(22) Nov. 15, 2005, pp. 8079-8088.
Extended European Search Report for European Patent Application No. 13806194.0 dated Apr. 4, 2016.
Toshiro Kageshita, "Akusei Kokushokushu No Atarashii Kessei Marker Glypican-3 To SPARC," Japanese Journal of Clinical Dermatology, Apr. 10, 2006, vol. 60, No. 5, pp. 169-172. English Translation.
International Preliminary Report on Patentability dated Dec. 31, 2014.

*Primary Examiner* — Alana Harris Dent
(74) *Attorney, Agent, or Firm* — Foley & Lardner LLP; Philippe Y. Riesen

(57) ABSTRACT

Provided is a kit for diagnosing at a high reproducibility, said kit being produced by preparing a monoclonal antibody against GPC3 and a monoclonal antibody against SPARC that are superior in quality stability to commercially available and commonly employed antibodies, and using these antibodies.

5 Claims, 15 Drawing Sheets

Fig. 1 Anti-SPARC monoclonal antibody
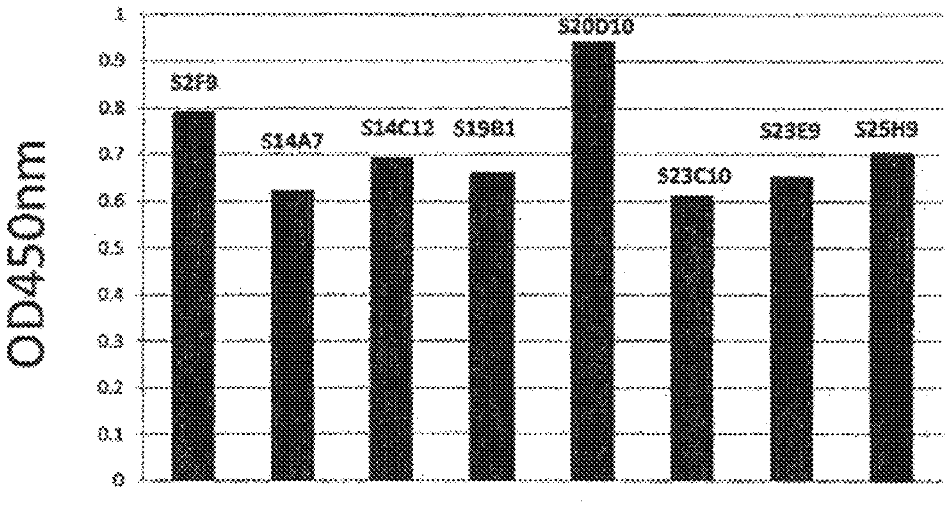
Fig. 2 Anti-GPC3 monoclonal antibody
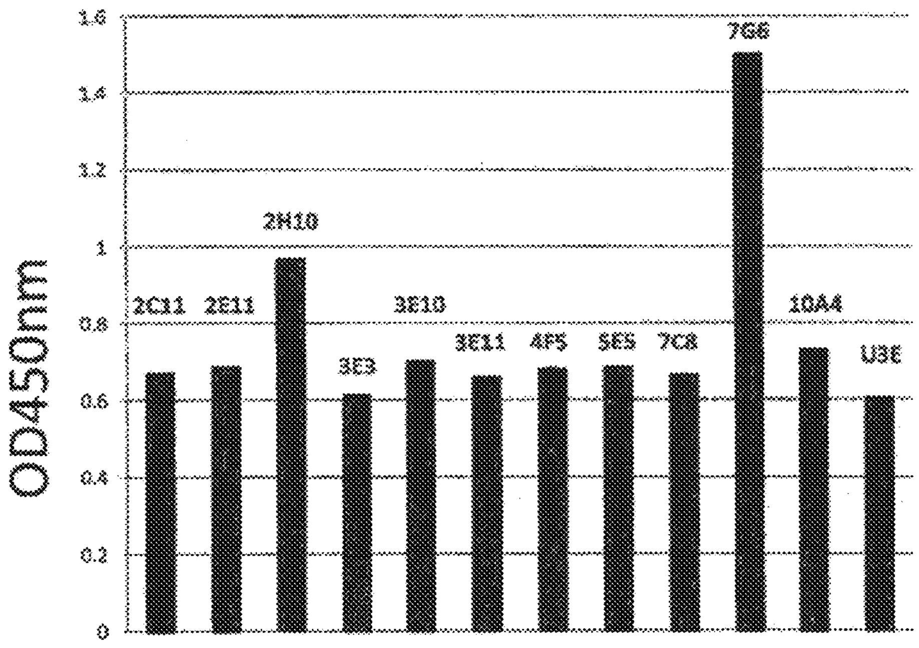

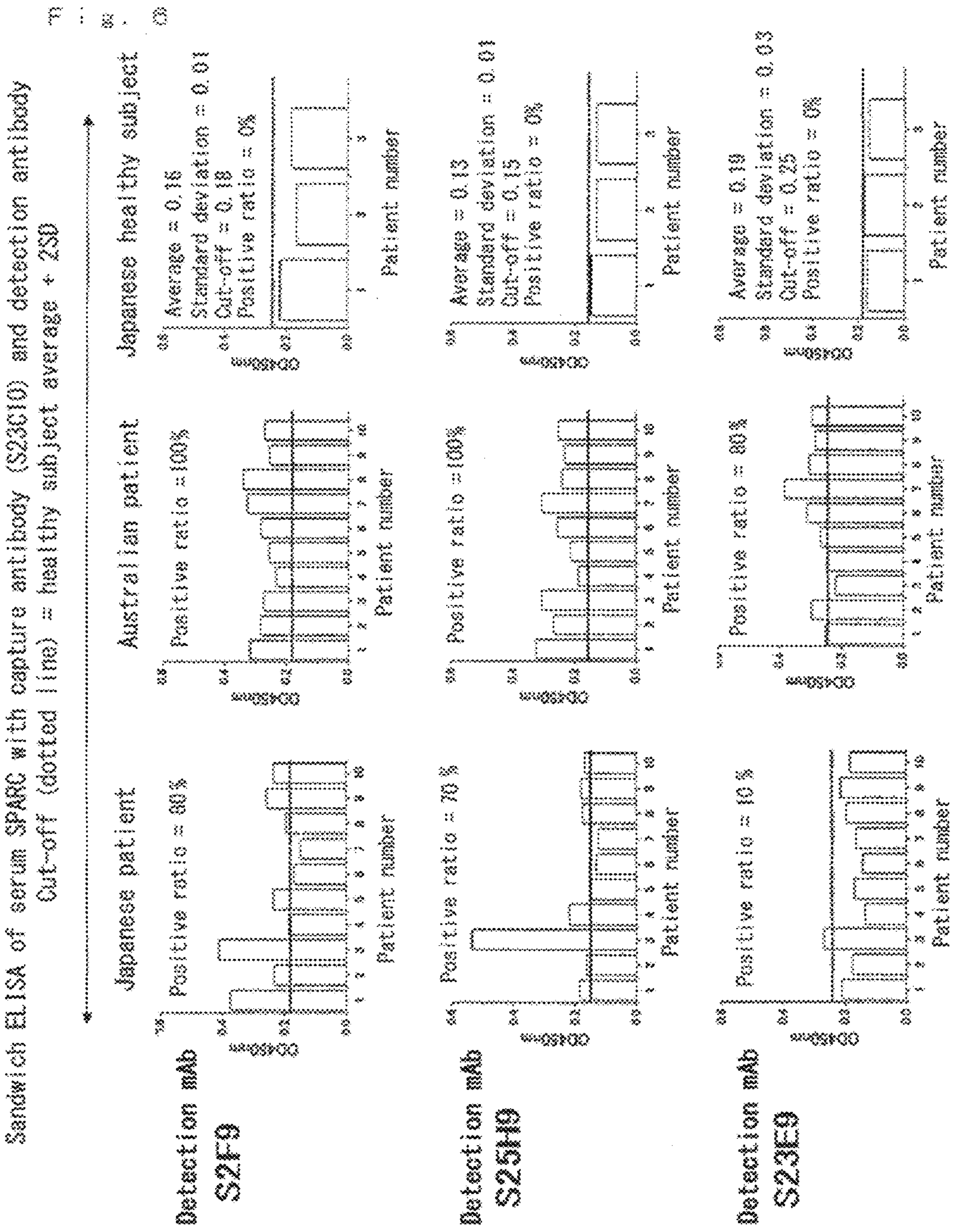
Fig. 6
Sandwich ELISA of serum SPARC with capture antibody (S23C10) and detection antibody
Cut-off (dotted line) = healthy subject average + 2SD
Japanese patient
Australian patient
Japanese healthy subject
Detection mAb S2F9
Positive ratio = 80%
Positive ratio =100%
Average = 0.16
Standard deviation = 0.01
Cut-off = 0.18
Positive ratio = 0%
Detection mAb S25H9
Positive ratio = 70%
Positive ratio =100%
Average = 0.13
Standard deviation = 0.01
Cut-off = 0.15
Positive ratio = 0%
Detection mAb S23E9
Positive ratio = 10%
Positive ratio = 80%
Average = 0.19
Standard deviation = 0.03
Cut-off = 0.25
Positive ratio = 0%
OD450nm
Patient number Setting of cut-off by serum GPC3 and SPARC values of 100 Japanese healthy subjects using sandwich ELISA using novel antibody

Fig. 8

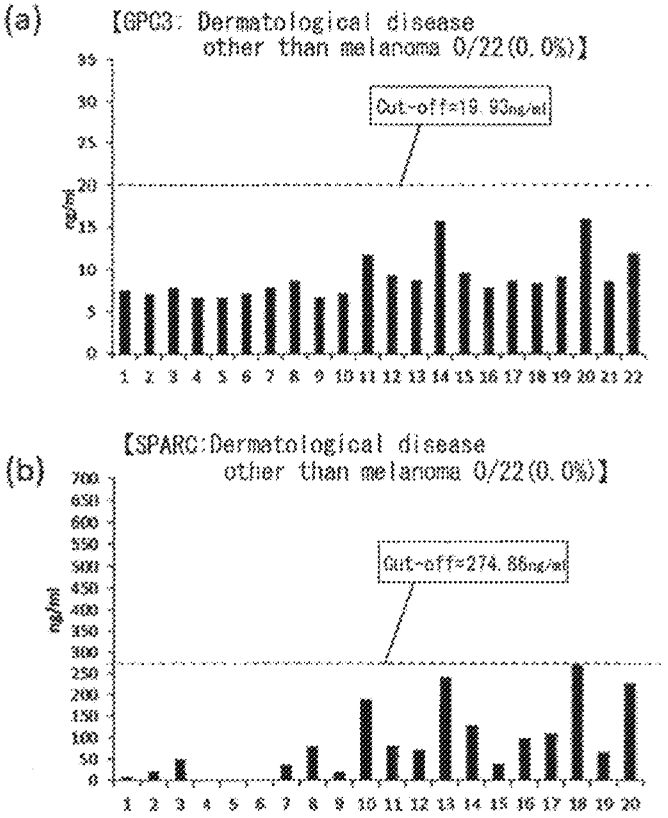

Comparative control group including dermatological disease

Expression:disease name[graph number]

Scleroderma (1),
Diabetes/hypertension (2),
Hydroa/diabetes/ischemic heart disease(3)
Drug rash (4),
Lyme disease (5),
Hydroa/hypertension/hyperlipemia(6),(9)
Erythema elevatum diutinum (7),
Hydroa/diabetes (8),
Hydroa/post-operation of breast cancer(10),
Atheroma (11),
Basal cell cancer (12),
Congenital pigmented nevus (13),
Eccrine poroma (14),
Pigmented nevus (15), (16), (19), (21),
Seborrheic keratosis (17), (20),
Merkel's cell cancer,extramammary
Paget disease(18),
Pyogenic granuloma (22)

GPC3 and SPARC values of Japanese 22 cases of dermatological disease other than melanoma Distribution of GPC3 values and SPARC values of Japanese patients of dermatological disease other than melanoma (n=22) and Japanese melanoma patients (n=56)

Positive ratio of GPC3 and SPARC according to melanoma disease types

Positive ratio of GPC3 and SPARC according to melanoma disease stages

Performance of sandwich ELISA using commercially available antibody for detecting GPC3 (according to disease types/disease stages)

Melanoma detection sensitivity by previous tumor marker LDH and 5-S-CD tests, which is classified according to disease types Melanoma detection sensitivity by previous tumor marker LDH and 5-S-CD tests, which is classified according to disease stages Distribution of GPC3 values and SPARC values of Australian healthy subjects (n=11) and Australian melanoma patients (n=28)

KIT FOR DIAGNOSING MALIGNANT MELANOMA

This application is a U.S. National Phase under 35 U.S.C. §371 of International Application PCT/JP2013/066631, filed on Jun. 17, 2013, which claims priority to Japanese Patent Application No. 2012-137019, filed on Jun. 18, 2012. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a novel kit for diagnosing malignant melanoma, a method of detecting malignant melanoma, and a novel monoclonal antibody used in the diagnostic kit.

BACKGROUND ART

Melanoma is one kind of a skin cancer called malignant melanoma. As the skin cancer, there are various kinds, and melanoma is a skin cancer having very high malignancy. A cell producing a melanin pigment, which exists in cells constituting a skin, is called a pigment cell (melanocyte), and the cell which has been cancerated is melanoma.

The incident number of melanoma in Japan is estimated to be about 1.5 to 2 persons per a population of 100000 persons, and it is presumed that about 1500 to 2000 persons develop melanoma annually. In Europe and the United States, the incident number is said to be ten-some or more persons per a population of 100000, and in Australia, the incident number of twenty-some or more persons per a population of 100000 is reported, and it is said that this is the highest incident number in the world. Therefore, peoples in Europe and the United States, and Australia, particularly, a white race is concerned with melanoma, and pays an attention to incidence of melanoma. Both in foreign countries and Japan, a tendency is recognized that incidence of melanoma is increased year by year. According to the certain search, it is reported that the number of deceased persons in one year due to this disease in Japan amounts to around 450 persons.

Peoples at any age develop melanoma, and particularly, when peoples become 40 years old or older, the incidence rate is increased, and the incidence rate becomes highest in their 60s to 70s. The incidence rate of infants is very small, but it cannot be said that infants do not develop melanoma, and there is recently a tendency that incidence in youths at their 20s to 30s is increased. Regarding the gender, there is no tendency that melanoma is frequent in either of a man or a woman, and melanoma is developed in both of a man and a woman. In Japanese, a site at which melanoma is easily developed is planta (sole of foot) in most cases, and the planta accounts for about 30%. It is the characteristic in Japanese that melanoma is also developed frequently at a part of a nail of a foot and a finger. In addition, like European and American peoples, melanoma is developed in a skin at any site such as the body, hand, foot, face and head.

On the other hand, measurement of a serum tumor marker is important not only in diagnosis of melanoma, but also in early detection of recurrence in postoperative cases, and determination of the therapeutic effect of advanced stage cases. As a tumor marker of melanoma, previously, usefulness of LDH and 5-S-cysteinyldopa (5-S-CD) of serum has been known, and further more recently, an S-100β protein and melanoma inhibitory activity (MIA) have been reported as more sensitive markers.

In Japan, as the existing tumor marker, 5-S-CD is mainly used, but these previously used tumor markers become positive only in a considerably advanced tumor such as Stage IV, and it must be said that usefulness is limited in respect of early diagnosis of melanoma, and early detection of postoperative recurrence.

The present inventors have conducted research regarding usefulness of GPC3 (glypican-3) and SPARC (Secreted protein, acidic rich in cysteine; another name osteonectin or BM-40) as a tumor marker, and previously reported that GPC3 and a combination of GPC3 and SPARC can be useful as a tumor marker of melanoma (Patent Documents 1 and 2).

However, in the method using an antibody to GPC3 described in Patent Document 1, the positive ratio of a melanoma patient is around 40%, and also in the method using a combination of an antibody to GPC3 and an antibody to SPARC described in Patent Document 2, the positive ratio of a melanoma patient is around 60%, and there is still room for improving detection sensitivity.

Further, since quality of commercially available antibodies which are usually used in detection of these tumor markers is not stable, low reproducibility is also a problem.

In addition, in the present description and drawings, particularly, in Examples, a novel monoclonal antibody provided by the present invention is called as a "novel antibody", and a method of the present invention using the novel antibody is called as a "novel method" in some cases. On the other hand, the commercially available anti-GPC3 antibody and anti-SPARC antibody which are usually used currently are called as a "commercially available antibody" in some cases. Further, serum LDH and 5-S-CD which have previously been used as the existing tumor marker are called as a "previous tumor marker" or an "existing tumor marker" in some cases. In addition, a method using these previous (existing) tumor markers is called as a "previous method" in some cases.

PRIOR ART DOCUMENTS

Patent Documents

Patent Document 1: WO2005/039380

Patent Document 2: WO2006/043362

DISCLOSURE OF INVENTION

Problems to be Solved by the Invention

One object of the present invention is to attempt sensitivity improvement of a diagnostic kit using an anti-GPC3 antibody or an anti-SPARC antibody in order to realize early diagnosis of melanoma.

A further object of the present invention is to make an anti-GPC3 monoclonal antibody and an anti-SPARC monoclonal antibody which are stable in quality as compared with the commercially available anti-GPC3 antibody and anti-SPARC antibody (commercially available antibodies), and provide a diagnostic kit having high reproducibility using the same.

Means for Solving the Problems

In view of the aforementioned objects, the present invention provides a novel monoclonal antibody for detecting GPC3 and SPARC which are a tumor marker useful in early diagnosis of melanoma, a kit for diagnosing melanoma using the novel antibody, and a method of detecting melanoma using the novel antibody.

That is, the present invention provides the following:

[1]: A kit for diagnosing malignant melanoma, comprising:

(1) a composition comprising one or more anti-GPC3 monoclonal antibodies selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E, produced by one or more hybridomas selected from the group consisting of clone names 2C11, 2E11, 2H10, 3E3, 3E10, 3E11, 4F5, 5E5, 7C8, 7G6, 10A4 and U3E, which were deposited at National Institute of Technology and Evaluation (NITE), NITE Patent Microorganisms Depositary (NPMD) on Apr. 23, 2012 under accession numbers NITE P-1326, NITE P-1327, NITE BP-01328, NITE P-1329, NITE BP-01330, NITE BP-01331, NITE P-1332, NITE P-1333, NITE P-1334, NITE P-1335, NITE P-1336 and NITE BP-01337, respectively, and (2) a composition comprising one or more anti-SPARC monoclonal antibodies selected from the group consisting of mAbS2F9, mAbS14A7, mAbS14C12, mAbS19B1, mAbS20D10, mAbS23C10, mAbS23E9 and mAbS25H9, produced by one or more hybridomas selected from the group consisting of clone names S2F9, S14A7, S14C12, S19B1, S20D10, S23C10, S23E9 and S25H9, which were deposited at NPMD on Apr. 23, 2012 under accession numbers NITE BP-01338, NITE P-1339, NITE P-1340, NITE P-1341, NITE P-1342, NITE BP-01343, NITE P-1344 and NITE BP-01345, respectively;

[2]: The diagnostic kit according to [1], wherein the anti-GPC3 monoclonal antibody is one or more selected from the group consisting of mAb2C11, mAb10A4, mAbU3E, mAb2H10, mAb3E3, mAb3E10 and mAb3E11, and the anti-SPARC monoclonal antibody is one or more selected from the group consisting of mAbS2F9, mAbS14C12, mAbS23C10, mAbS23E9 and mAbS25H9;

[3]: The diagnostic kit according to [1] or [2], wherein the anti-GPC3 monoclonal antibody is one or more selected from the group consisting of mAbU3E, mAb2H10, mAb3E10, mAb3E11 and mAb3E3, and the anti-SPARC monoclonal antibody is one or more selected from the group consisting of mAbS23C10, mAbS2F9, mAbS25H9 and mAbS23E9;

[4]: The diagnostic kit according to any one of [1] to [3], which is provided in a form of an ELISA kit;

[5]: The diagnostic kit according to [4], which is provided in a form of a sandwich ELISA kit;

[6]: The diagnostic kit according to [5], wherein a capture antibody in the sandwich ELISA method using an anti-GPC3 monoclonal antibody is selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E, and a detection antibody is one or more selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E, all being different from the capture antibody, and a capture antibody in the sandwich ELISA method using an anti-SPARC monoclonal antibody is selected from the group consisting of mAbS2F9, mAbS14A7, mAbS14C12, mAbS19B1, mAbS20D10, mAbS23C10, mAbS23E9 and mAbS25H9, and a detection antibody is one or more selected from the group consisting of mAbS2F9, mAbS14A7, mAbS14C12, mAbS19B1, mAbS20D10, mAbS23C10, mAbS23E9 and mAbS25H9, all being different from the capture antibody;

[7]: The diagnostic kit according to [5] or [6], wherein the capture antibody in the sandwich ELISA method using the anti-GPC3 monoclonal antibody is selected from the group consisting of mAb2C11, mAb10A4, mAbU3E and mAb3E11, and the detection antibody is one or more selected from the group consisting of mAb2H10, mAb3E3 and mAb3E10, the capture antibody in the sandwich ELISA method using the anti-SPARC monoclonal antibody is selected from the group consisting of mAbS2F9, mAbS14C12 and mAbS23C10, and the detection antibody is one or more selected from the group consisting of mAbS2F9, mAbS23C10, mAbS23E9 and mAbS25H9, all being different from the capture antibody;

[8]: The diagnostic kit according to any one of [5] to [7], wherein the capture antibody in the sandwich ELISA method using the anti-GPC3 monoclonal antibody is mAbU3E or mAb3E11, and the capture antibody in the sandwich ELISA method using the anti-SPARC monoclonal antibody is mAbS23C10 or mAbS2F9;

[9]: The diagnostic kit according to any one of [5] to [8], wherein the capture antibody in the sandwich ELISA method using the anti-GPC3 monoclonal antibody is either mAbU3E or mAb3E11, and the detection antibody is one or more selected from the group consisting of mAb2H10, mAb3E10 and mAb3E3, the capture antibody in the sandwich ELISA method using the anti-SPARC monoclonal antibody is either mAbS2F9 or mAbS23C10, and the detection antibody is one or more selected from the group consisting of mAbS2F9, mAbS23C10, mAbS25H9 and mAbS23E9, all being different from the capture antibody;

[10]: The diagnostic kit according to any one of [1] to [9], which is used for a blood, serum or plasma sample of a subject;

[11]: The diagnostic kit according to [10], wherein the subject is a white race;

[12]: A method of detecting malignant melanoma, comprising contacting (1) a composition comprising one or more anti-GPC3 monoclonal antibodies selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E as defined in [1], and (2) a composition comprising one or more anti-SPARC monoclonal antibodies selected from the group consisting of mAbS2F9, mAbS14A7, mAbS14C12, mAbS19B1, mAbS20D10, mAbS23C10, mAbS23E9 and mAbS25H9 as defined in [1], with a sample from a subject;

[13]: The detection method according to [12], wherein the sample is blood, serum or plasma of a subject;

[14]: The detection method according to [13], wherein the subject is a white race;

[15]: The detection method according to any one of [12] to [14], which is performed by an ELISA method;

[16]: The detection method according to [12], which is performed by an immunostaining method;

[17]: An anti-GPC3 monoclonal antibody selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E as defined in [1];

[18]: The anti-GPC3 monoclonal antibody according to [1]7, which is selected from the group consisting of mAb2H10, mAb3E10, mAb3E11, mAbU3E and mAb3E3;

[19]: An anti-SPARC monoclonal antibody selected from the group consisting of mAbS2F9, mAbS14A7, mAbS14C12, mAbS19B1, mAbS20D10, mAbS23C10, mAbS23E9 and mAbS25H9 as defined in [1];

[20]: The anti-SPARC monoclonal antibody according to [19], which is selected from the group consisting of mAbS2F9, mAbS23C10, mAbS25H9 and mAbS23E9;

[21]: A hybridoma selected from the group consisting of clone names 2C11, 2E11, 2H10, 3E3, 3E10, 3E11, 4F5, 5E5, 7C8, 7G6, 10A4 and U3E, which were deposited at NPMD on Apr. 23, 2012 under accession numbers NITE P-1326, NITE P-1327, NITE BP-01328, NITE P-1329, NITE BP-01330, NITE BP-01331, NITE P-1332, NITE P-1333, NITE P-1334, NITE P-1335, NITE P-1336 and NITE BP-01337, respectively, as defined in [1];

[22]: The hybridoma according to [21], which is selected from the group consisting of clone names 2H10, 3E10, 3E11, U3E and 3E3;

[23]: A hybridoma selected from the group consisting of clone names S2F9, S14A7, S14C12, S19B1, S20D10, S23C10, S23E9 and S25H9, which were deposited at NPMD on Apr. 23, 2012 under accession numbers NITE BP-01338, NITE P-1339, NITE P-1340, NITE P-1341, NITE P-1342, NITE BP-01343, NITE P-1344 and NITE BP-01345, respectively, as defined in [1]; and

[24]: The hybridoma according to [23], which is selected from the group consisting of clone names S2F9, S23C10, S25H9 and S23E9.

Explanation of Deposition

In the present description, as summarized in Table 10, among hybridomas provided by the present invention, clones 2C11 (Japanese domestic accession number NITE P-1326), 2E11 (the same NITE P-1327), 4F5 (the same NITE P-1332), 5E5 (the same NITE P-1333), 7C8 (the same NITE P-1334), 7G6 (the same NITE P-1335), 10A4 (the same NITE P-1336), S14A7 (the same NITE P-1339), S14C12 (the same NITE P-1340), S19B1 (the same NITE P-1341), and S20D10 (the same NITE P-1342) were deposited domestically in Japan at National Institute of Technology and Evaluation (NITE), NITE Patent Microorganisms Depositary (NPMD) on Apr. 23, 2012, and deposition in Japan is continuing. On the other hand, regarding clones 2H10 (international accession number NITE BP-01328), 3E10 (the same NITE BP-01330), 3E11 (the same NITE BP-01331), U3E (the same NITE BP-01337), S2F9 (the same NITE BP-01338), S23C10 (the same NITE BP-01343), and S25H9 (the same NITE BP-01345), all were deposited domestically in Japan at NPMD on Apr. 23, 2012, thereafter, transfer to international deposition based on Budapest Treaty was requested on Apr. 1, 2013, and receipts of deposit concerning international deposition were issued on Jun. 7, 2013. Further, regarding clones 3E3 (domestic accession number NITE P-1329) and S23E9 (domestic accession number NITE P-1344), both were deposited domestically in Japan at NPMD on Apr. 23, 2012, thereafter, transfer to international deposition based on Budapest Treaty was requested on Jun. 12, 2013, but receipts of deposit concerning international deposition have not yet been issued at the international filing date of the present application. Regarding these two clones, after success in a test for finding the clones to be alive, receipts of deposit concerning international deposition, which will be given international accession numbers of NITE BP-01329 and NITE BP-01344, respectively, are scheduled to be issued.

Effect of the Invention

A kit for diagnosing melanoma including a combination of novel monoclonal antibodies made by the present invention, when it is provided as, for example, a sandwich ELISA kit, is usually more highly sensitive than when commercially available antibodies which are used for GPC3 and SPARC are combined. In a kit for diagnosing melanoma and a method of detecting melanoma using the monoclonal antibody of the present invention, the positive ratio in diagnosis of melanoma at an early stage is very high, and the kit and the method are very useful for conducting precise diagnosis of melanoma at an early stage. Further, in the monoclonal antibody made by the present invention, false positive is almost eliminated, and specificity is high, in diagnosis and detection of melanoma.

Further, according to the present invention, differential diagnosis between melanoma and other skin disease is possible. In addition, the novel antibody of the present invention shows excellent detection sensitivity as compared with a commercially available antibody. Further, according to the present invention, diagnosis is more excellent than previous diagnosis with LDH or 5-S-CD, either in whole melanoma, or in diagnosis of ALM (acral lentiginous melanoma) and SSM (superficial spreading melanoma). Further, regardless of an advanced stage of melanoma, according to the method of the present invention, diagnosis of melanoma is possible, and cases at an early stage which cannot be determined by the previous method such as an LDH test can be diagnosed according to the method of the present invention. Particularly, at the stage 0-1 in which possibility of complete cure is as high as almost 100%, the excellent diagnosis result is obtained by the method of the present invention.

BRIEF DESCRIPTION OF DRAWINGS

FIG. 1 shows an ELISA data of a purified anti-SPARC monoclonal antibody.

FIG. 2 shows an ELISA data of a purified anti-GPC3 monoclonal antibody.

FIG. 6 shows the result of sandwich ELISA of serum SPARC when mAbS23C10 is used as a capture antibody.

FIG. 8 shows GPC3 (a) and SPARC (b) values of 22 Japanese cases of a dermatological disease other than melanoma.

FIG. 16 shows distributions of GPC3 values (a) and SPARC values (b) of Australian healthy subjects (n=11) and Australian melanoma patients (n–28).

BEST MODE FOR CARRYING OUT THE INVENTION

Figure 3:
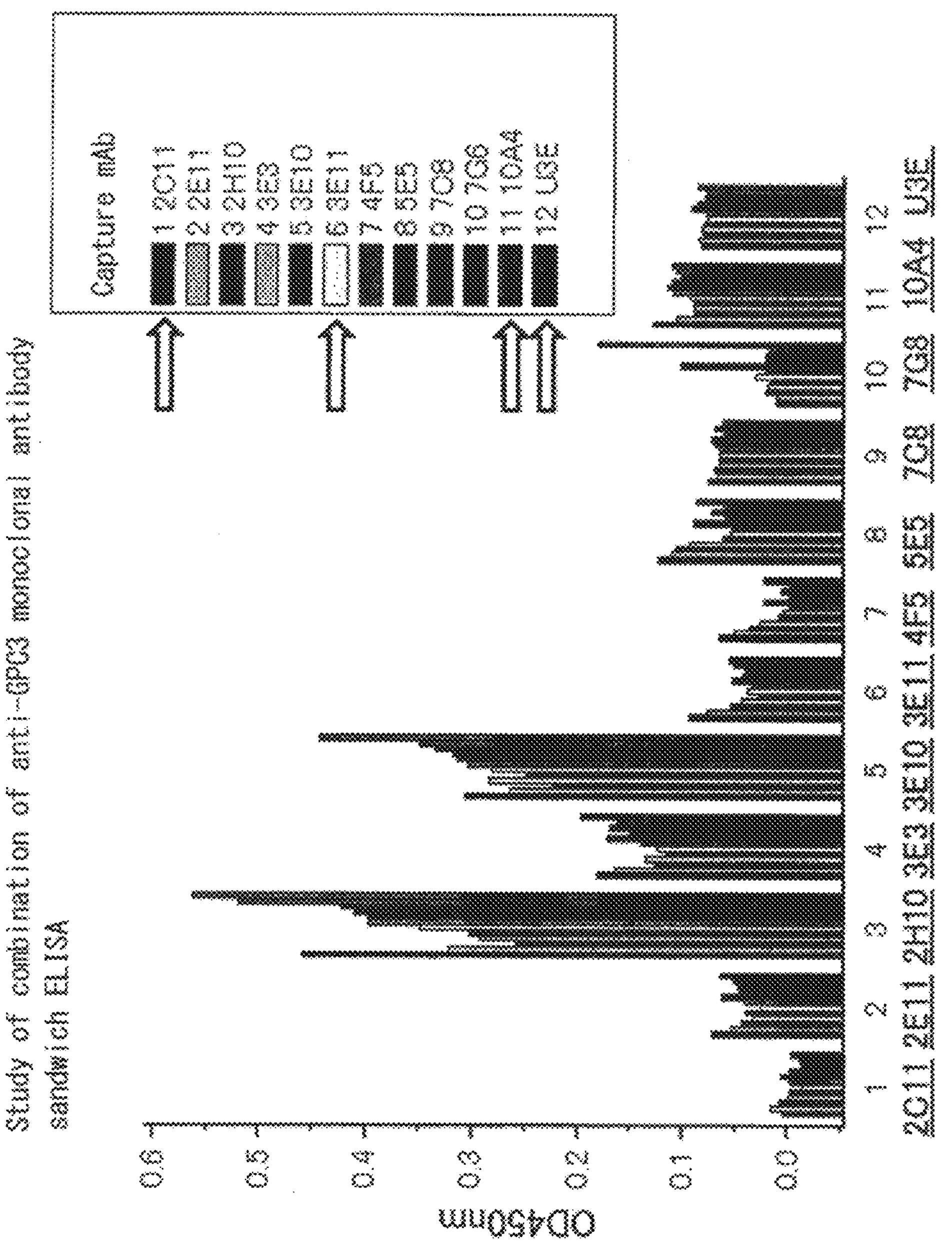
FIG. 3 shows the result of study of a combination of antibodies for sandwich ELISA concerning an anti-GPC3 monoclonal antibody.

A specific aspect of the present invention will be explained below, and first, a novel anti-GPC3 monoclonal antibody and a novel anti-SPARC monoclonal antibody which are used in the present invention will be explained.

An anti-GPC3 monoclonal antibody used in the present invention is an anti-GPC3 monoclonal antibody produced by a hybridoma (clone name), 2C11, 2E11, 2H10, 3E3, 3E10, 3E11, 4F5, 5E5, 7C8, 7G6, 10A4 or U3E, which is a fused cell of a mouse spleen cell and a mouse myeloma. The hybridomas were deposited at National Institute of Technology and Evaluation (NITE), NITE Patent Microorganisms Depositary (NPMD) (simply referred to as NPMD in some cases, in the present description and claims) on April 23 in Heisei 24 Year (2012), and accession numbers NITE P-1326, NITE P-1327, NITE BP-01328, NITE P-1329 (international accession number NITE BP-01329 is scheduled to be issued after the international filing date), NITE BP-01330, NITE BP-01331, NITE P-1332, NITE P-1333, NITE P-1334, NITE P-1335, NITE P-1336 and NITE BP-01337 were given, respectively. In addition, for details of domestic deposition and international deposition, see the paragraph following the header "Explanation of depostion" above and Table 10 later.

On the other hand, an anti-SPARC monoclonal antibody used in the present invention is an anti-SPARC monoclonal antibody which is produced by a hybridoma (clone name), S2F9, S14A7, S14C12, S19B1, S20D10, S23C10, S23E9 or S25H9, which is a fused cell of a mouse spleen cell and a mouse myeloma. The hybridomas were deposited at NPMD on April 23 in Heisei 24 Year (2012), and accession numbers NITE BP-01338, NITE P-1339, NITE P-1340, NITE P-1341, NITE P-1342, NITE BP-01343, NITE P-1344 (international accession number NITE BP-01344 is scheduled to be given after the international filing date) and NITE BP-02345 were given, respectively. In addition, for details of domestic deposition and international deposition, see the paragraph following the header "Explantion of deposition" above and Table 10 later.

In the present description and claims, the hybridomas are referred to simply by respective clone names in some cases. On the other hand, respective monoclonal antibodies which are produced by the hybridomas are represented by adding "mAb", which is abbreviation representing a monoclonal antibody, before the clone name of the hybridoma producing it.

That is, anti-GPC3 monoclonal antibodies produced by hybridomas named as clone names 2C11, 2E11, 2H10, 3E3, 3E10, 3E11, 4F5, 5E5, 7C8, 7G6, 10A4 and U3E, which were deposited at NPMD under accession numbers NITE P-1326, NITE P-1327, NITE BP-01328, NITE P-1329, NITE BP-01330, NITE BP-01331, NITE P-1332, NITE P-1333, NITE P-1334, NITE P-1335, NITE P-1336 and NITE BP-01337, respectively, are named as mAb2C11, mAb2E11, mAb2H10, mAb3E3, mAb3E10, mAb3E11, mAb4F5, mAb5E5, mAb7C8, mAb7G6, mAb10A4 and mAbU3E, respectively, and anti-SPARC monoclonal antibodies produced by hybridomas named as clone names S2F9, S14A7, S14C12, 319B1, S20D10, S23C10, S23E9 and S25H9, which were deposited at NPMD under accession numbers NITE BP-01338, NITE P-1339, NITE P-1340, NITE P-1341, NITE P-1342, NITE BP-01343, NITE P-1344 and NITE BP-01345, respectively, are named as mAbS2F9, mAbS14A7, mAbS14C12, mAbS19B1, mAbS20D10, mAbS23C10, mAbS23E9 and mAbS25H9, respectively. However, in Examples and the drawings, for simplicity, each monoclonal antibody is specified only by the aforementioned clone name of the hybridoma producing each monoclonal antibody by omitting "mAb" from the aforementioned name of each monoclonal antibody, in some cases.

In addition, in the present description and claims, as a general term for the aforementioned mAb2C11, mAb2E11, mAb2H10, mAb3E3, mAb3E10, mAb3E11, mAb4F5, mAb5E5, mAb7C8, mAb7G6, mAb10A4 and mAbU3E, "anti-GPC3 monoclonal antibody" or "anti-GPC3mAb" is employed, or simply "anti-GPC3 antibody" is used in some cases. Similarly, as a general term for the aforementioned mAbS2F9, mAbS14A7, mAbS14C12, mAbS19B1, mAbS20D10, mAbS23C10, mAbS23E9 and mAbS25H9, "anti-SPARC monoclonal antibody" or "anti-SPARCmAb" is employed, or simply "anti-SPARC antibody" is used in some case.

In the present description and claims, the anti-GPC3 monoclonal antibody and the anti-SPARC monoclonal antibody include a fragment, and an altered antibody such as a chimeric antibody and a humanized antibody, as well as a variant antibody, of each of them. Examples of the fragment of an antibody include a $F(ab')_2$ fragment, and a Fab fragment. The fragment, altered antibody and variant antibody also have specificity for a GPC3 or SPARC protein, respectively, like the original anti-GPC3 monoclonal antibody or anti-SPARC monoclonal antibody. These can be produced by the means or methods which are well-known to a person skilled in the art.

Then, a method of obtaining the anti-GPC3 monoclonal antibody and the anti-SPARC monoclonal antibody used in the present invention will be explained.

An amino acid sequence of a human GPC3 protein used for obtaining the anti-GPC3 monoclonal antibody is publicly known, and registered in, for example, protein database of GenBank as Accession No. NP_004475, and a person skilled in the art can easily obtain it. On the other hand, an amino acid sequence of a human SPARC protein used for obtaining the anti-SPARC monoclonal antibody is publicly known, and registered in, for example, protein database of GenBank as Accession No. NM_003118, and a person skilled in the art can easily obtain it.

The anti-GPC3 monoclonal antibody and the anti-SPARC monoclonal antibody of the present invention can be obtained by, for example, immunizing a mammal such as a mouse with a GPC3 protein or a fragment thereof or a SPARC protein or a fragment thereof, respectively, fusing a spleen cell of the immunized animal and a myeloma to make a hybridoma, and culturing this. On the other hand, such a monoclonal antibody may be produced using other method which is well-known to a person skilled in the art, for example, a gene recombinant method, a chemical synthesis method or the like. In addition, the monoclonal antibody for the present invention may be an antibody recognizing any epitope of GPC3 or SPARC.

Specifically, as described in Examples later, in order to make monoclonal antibodies to GPC3 and SPARC, a GPC3 protein or a SPARC protein was mixed with a Freund's incomplete adjuvant or TiterMax GOLD (TiterMAX) which is an artificial adjuvant to prepare an emulsion, this was immunized into a inguinal region lymph node or a footpad of a BALB/c mouse, and frequent immunization was performed. After final immunization, a spleen was collected, and a spleen B cell and a myeloma were subjected to cell fusion using PEG1500 (Roche). Selective culturing of a hybridoma in a RPMI1640 medium in the presence of HAT (Invitrogen) was performed for 2 weeks to select a fused cell. Further, an antibody which had been secreted in the culturing supernatant was screened by ELISA covered with GPC3 or SPARC, to select a hybridoma producing an antibody. By culturing the hybridoma under the culturing condition well-known to a person skilled in the art, the anti-GPC3 monoclonal antibody and the anti-SPARC monoclonal antibody of the present invention can be obtained. In addition, the resulting monoclonal antibody can be purified as follows.

The culturing supernatant obtained by culturing a hybridoma producing an intended antibody, or a hybridoma is inoculated into an abdominal cavity of a BALB/c or nude mouse, and a monoclonal antibody is purified from ascites obtained after a few weeks. Purification of an antibody can be performed by affinity purification using Protein A-conjugated Sepharose (GE Healthcare) or Protein G-conjugated Sepharose (GE Healthcare). Alternatively, GPC3 or SPARC can also be purified by an antigen column prepared by immobilization on a ligand coupling carrier, such as CNBr-activated Sepharose 4B (GE Healthcare).

Then, a specific aspect of the present invention will be explained in detail.

In first aspect, the present invention provides the kit for diagnosing malignant melanoma described in above [1]. The diagnostic kit essentially includes (1) a composition comprising one or more anti-GPC3 monoclonal antibodies selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E (hereinafter, also referred to as composition (1)), and (2) a composition comprising one or more anti-SPARC monoclonal antibodies selected from the group consisting of mAbS2F9, mAbS14A7, mAbS14C12, mAbS19B1, mAbS20D10, mAbS23C10, mAbS23E9 and mAbS25H9 (hereinafter, also referred to as composition (2)). The kit of the present invention may appropriately include, for example, a sample collecting means, a label, a reactor, a reagent for detection (e.g. secondary antibody, a coloring reagent, buffer etc.) and the like, in addition to the composition (1) and the composition (2). Specifically, for example, the kit of the present invention may include a reagent necessary for ELISA such as a sandwich method, a competition method, a direct adsorption method and the like, or a reagent necessary for conducting analysis such as a Western blotting method and the like. Generally, an instruction manual is added to the kit.

The composition (1) and the composition (2) contained in the kit of the present invention essentially comprise one or more anti-GPC3 monoclonal antibodies selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E, and one or more anti-SPARC monoclonal antibodies selected from the group consisting of mAbS2F9, mAbS14A7, mAbS14C12, mAbS19B1, mAbS20D10, mAbS23C10, mAbS23E9 and mAbS25H9, respectively. The anti-GPC3 monoclonal antibody or the SPARC monoclonal antibody contained in each composition may be one kind, or two or more kinds, respectively. By containing two or more monoclonal antibodies, sensitivity, specificity and precision of the diagnostic kit of the present invention can be improved.

In the kit of the present invention, the anti-GPC3 monoclonal antibody and the anti-SPARC monoclonal antibody contained in the composition (1) and the composition (2) may be labeled. A variety of labels are well-known to a person skilled in the art, and can be appropriately selected. Examples of the label include labels such as chemical substances such as biotin, digoxigenin (DIG), acridium ester, Flashlight and the like, enzymes such as horseradish peroxidase (HRP), ALP, glucose oxidase, β-galactosidase and the like, fluorescent labels such as FITC, rhodamine, Cy3, Cy5, Texas Red, Alexa Flucors, BODIPYs, IRDyes, MFPs, Quantum Dots, AMCA, Allophycocyanin, BMP, Cy2, Cy3.5, Cy5.5, DTAF, DyLight 547, DyLight 647, FluoroNanogold, phycoerythrin, phycocyanin, R-PE, saporin, TRITC and the like, beads such as 60 mm Micro-bead, magnetic beads such as MagCellect Ferrofluid (registered trademark), radioactive labels such as $^{123}$I, gold particle, agarose and the like.

Further, the composition (1) and the composition (2) contained in the kit of the present invention may comprise a variety of substances such as a buffer, a medium component, an excipient, an additive and a carrier, if necessary, in addition to the anti-GPC3 monoclonal antibody or the anti-SPARC monoclonal antibody.

The concentration of the optionally labeled anti-GPC3 monoclonal antibody or anti-SPARC monoclonal antibody, which is contained in the composition (1) and the composition (2) contained in the kit of the present invention is not particularly limited, but can be appropriately selected depending on the form of the kit or the like. For example, monoclonal antibodies can be used at a concentration of around 0.1 to 10 μg/ml in the composition, respectively.

From the view point of specificity for an antigen and sensitivity of detection of melanoma, a preferable anti-GPC3 monoclonal antibody contained in the composition (1) contained in the kit of the present invention is one or more selected from the group consisting of mAb2C11, mAb10A4, mAbU3E, mAb2H10, mAb3E3, mAb3E10 and mAb3E11, and a preferable anti-SPARC monoclonal antibody contained in the composition (2) is one or more selected from the group consisting of mAbS2F9, mAbS14C12, mAbS23C10, mAbS23E9 and mAbS25H9.

Further preferably, the anti-GPC3 monoclonal antibody is one or more selected from the group consisting of mAbU3E, mAb2H10, mAb3E10, mAb3E11 and mAb3E3. In addition, a further preferable anti-SPARC monoclonal antibody is one or more selected from the group consisting of mAbS23C10, mAbS2F9, mAbS25H9 and mAbS23E9.

Examples of a method of diagnosis or detection which is adopted in the kit of the present invention include an ELISA method such as a sandwich ELISA method, an immunoblotting method, a radioimmunoassay (RIA) method, an immunoprecipitation method, a method using a protein array, a method using a flow cytometer, a chemiluminescence enzyme immunoassay method (CLEIA), a bioluminescence enzyme immunoassay method (BLEIA), a measuring method using a developing equipment which can be transfused by capillary phenomenon (test piece for immunoassay), an immunochromatography method, an immunostaining method, an agglutination method and the like.

In the present invention, the diagnostic kit is provided preferably in a form of an ELISA kit, further preferably in a form of a sandwich ELISA kit. The ELISA kit does not necessitate a special facility, and can conduct an antigen-antibody reaction rapidly and easily. In the sandwich ELISA kit, it is necessary that two kinds of antibodies which recognize the same protein with different epitopes are used, and this is particularly preferable in respect of very high specificity, due to the property that the same protein is detected using two kinds of antibodies of a capture antibody and a detection antibody.

Specifically, for example, in the sandwich ELISA, two kinds of antibodies having different antigen recognition sites are prepared, and one antibody (capture antibody) is adsorbed onto a plate. A sample is contacted with the plate to perform a reaction, further, the other antibody (detection antibody) having a different antigen recognition site is reacted, and binding of the detection antibody is detected by use of a label or the like. In detection of the binding of the detection antibody, for example, as described in Examples, the detection antibody is biotinylated, the biotinylated detection antibody is added and, thereafter, a complex of enzymes such as (strept)avidin and horseradish peroxidase is added to the plate. Then, after a substrate which develops a color by an enzyme is added to perform a coloring reaction, the coloring intensity is measured with a spectrophotometer, thereby, detection or measurement of GPC3 and SPARC in a sample can be performed. As a label to be bound to the detection antibody, biotin is representative, but other label may be used, or an enzyme may be directly bound.

In the case where the diagnostic kit of the present invention is provided in a form of sandwich ELISA, it is preferable that a capture antibody in the sandwich ELISA method using the anti-GPC3 monoclonal antibody is selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E, and the detection antibody is one or more selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E, all being different from the capture antibody, and a capture antibody in the sandwich ELISA method using the anti-SPARC monoclonal antibody is selected from the group consisting of mAbS2F9, mAbS14A7, mAbS14C12, mAbS19B1, mAbS20D1, mAbS23C10, mAbS23E9 and mAbS25H9, and a detection antibody is one or more selected from the group consisting of mAbS2F9, mAbS14A7, mAbS14C12, mAbS19B1, mAbS20D10, mAbS23C10, mAbS23E9 and mAbS25H9, all being different from the capture antibody. In addition, as the detection antibody, one kind of mAb may be used, or a cocktail obtained by mixing two or more kinds of mAbs may be used.

In the case where the diagnostic kit of the present invention is provided in a form of sandwich ELISA, from the view point of specificity and detection sensitivity, it is more preferable that a capture antibody in the sandwich ELISA method using the anti-GPC3 monoclonal antibody is selected from the group consisting of mAb2C11, mAb10A4, mAbU3E and mAb3E11, and a detection antibody is one or more selected from the group consisting of mAb2H10, mAb3E3 and mAb3E10, and a capture antibody in the sandwich ELISA method using the anti-SPARC monoclonal antibody is selected from the group consisting of mAbS2F9, mAbS14C12 and mAbS23C10, and a detection antibody is one or more selected from the group consisting of mAbS2F9, mAbS23C10, mAbS23E9 and mAbS25H9, all being different from the capture antibody, and it is further preferable that a capture antibody in the sandwich ELISA method using the anti-GPC3 monoclonal antibody is mAbU3E or mAb3E11, and a capture antibody in the sandwich ELISA method using the anti-SPARC monoclonal antibody is mAbS23C10 or mAbS2F9.

Further, in the diagnostic kit of the present invention, it is particularly preferred that the capture antibody in the sandwich ELISA method using the anti-GPC3 monoclonal antibody is either mAbU3E or mAb3E11, and the detection antibody is one or more selected from the group consisting of mAb2H10, mAb3E10 and mAb3E3, the capture antibody in the sandwich ELISA method using the anti-SPARC monoclonal antibody is either mAbS2F9 or mAbS23C10, and the detection antibody is one or more selected from the group consisting of mAbS2F9, mAbS23C10, mAbS25H9 and mAbS23E9, all being different from the capture antibody.

A sample which is analyzed by the diagnostic kit of the present invention is not particularly limited, and may be any sample in which a GPC3 protein and/or a SPARC protein may be contained. Preferably, the sample is a blood, serum or plasma sample of a subject.

In addition, a subject is also not particularly limited, and may be a subject in any area in the world including Japanese, Australians, Europeans and Americans, and from the view point of the positive ratio, particularly, it is preferable that the subject is a white race such as Australian and the like.

By using the diagnostic kit of the present invention, early diagnosis of melanoma can be performed specifically and at the high positive ratio.

In a second aspect, the present invention provides a method of detecting malignant melanoma including contacting a composition comprising an anti-GPC3 monoclonal antibody (composition (1)) and a composition comprising an anti-SPARC monoclonal antibody (composition (2)), which were described in above [12] and detailed in the first aspect, with a sample from a subject.

In the detection method of the present invention, the presence or amount of SPARC and GPC3 in a sample can be detected by contacting a sample with a composition comprising an anti-GPC3 monoclonal antibody (composition (1)), and contacting a sample with a composition comprising an anti-SPARC monoclonal antibody (composition (2)). The presence of SPARC and/or GPC3 in a sample is an index that a subject is affected with malignant melanoma.

Contact between the sample with the composition (1) and the composition (2) may be performed based on the method which is usually performed in the art, and is not particularly limited. The detection method of the present invention is performed preferably in vitro.

Detection of binding of a GPC3 protein and/or a SPARC protein present in a sample with the anti-GPC3 monoclonal antibody and/or the anti-SPARC monoclonal antibody of the present invention may be performed by any method well-known to a person skilled in the art, and specifically, examples include detection means described in the first aspect. In addition, both of the anti-GPC3 monoclonal antibody and the anti-SPARC monoclonal antibody contained in the composition (1) and the composition (2) used in the detection method of the present invention may be antibodies which have been appropriately labeled depending on a means for detecting an antigen-antibody reaction. The label may be any label well-known to a person skilled in the art, and specifically, examples include labels described in the first aspect.

For example, in order to detect the presence or amount of GPC3 and/or SPARC in a sample by the detection method of the present invention, it is only necessary to react a sample and the anti-GPC3 monoclonal antibody and the anti-SPARC monoclonal antibody contained in the composition (1) and the composition (2), and detect a complex which is a reaction product. By binding a label such as an enzyme, a radioactive substance, a fluorescent substance and the like to an antibody in advance, it becomes possible to detect a complex which is a reaction product. Specifically, for example, an index for diagnosing whether a subject is affected with malignant melanoma or not is obtained, by detecting the presence or amount of GPC3 and/or SPARC by the known detection/measurement method such as ELISA such as a sandwich method, a competition method, a direct adsorption method and the like, an agglutination method, or a Western blotting method.

In addition, a reaction for detection may be performed in a liquid phase such as a well and the like, or may be performed on a solid phase support on which the anti-GPC3 monoclonal antibody or the anti-SPARC monoclonal antibody is immobilized. In this case, by comparison with a standard value which has been produced in advance using a normal sample which is not affected with melanoma, or a sample which has been found to be melanoma, whether a measured value is melanoma-positive or not can be determined. In addition, upon detection, it is preferable to set a cut-off value by measuring the amount of GPC3 and SPARC in serum of many melanoma patients and healthy subjects.

A sample to be subjected to the detection method of the present invention is not particularly limited, and may be any sample, and preferably, examples include a body fluid such as blood, saliva or urine, or a skin tissue piece or the like, obtained from a subject who may be affected with melanoma, and the sample is particularly preferably blood, serum or plasma of a subject.

For example, when a skin tissue piece is a sample, malignant melanoma can be detected by performing immunostaining of an organ tissue piece prepared according to a usual method using the anti-GPC3 monoclonal antibody and the anti-SPARC monoclonal antibody contained in the composition (1) and the composition (2) of the present invention, respectively, and seeing the presence or absence of expression of GPC3 and SPARC.

On the other hand, when a body fluid such as blood, serum or plasma of a subject is a sample, for example, after contact of a sample with the anti-GPC3 monoclonal antibody and the anti-SPARC monoclonal antibody which are contained in the composition (1) and the composition (2) of the present invention, respectively, specific binding of GPC3 and/or SPARC which can be present in a sample and an antibody can be detected using a label such as a fluorescent substance, a light emitting substance, an enzyme and the like.

A subject to be subjected to the detection method of the present invention is not also particularly limited, and may be a subject in any area in the world including Japanese, Australians, Europeans and Americans, and from the view point of the positive ratio, particularly, a white race such as Australian is preferable.

As described above, in the detection method of the present invention, detection of binding of a GPC3 protein and/or a SPARC protein present in a sample, and the anti-GPC3 monoclonal antibody and/or the anti-SPARC monoclonal antibody of the present invention may be performed by any method well-known to a person skilled in the art, and specifically, examples include the detection means described in the first aspect.

Among the detection means described in the first aspect, the ELISA method is preferably used since it does not necessitate a special facility, and can detect the presence or amount of a GPC3 protein and/or a SPARC protein rapidly and easily. Among the ELISA method, the sandwich ELISA method is particularly preferable, as described above.

In the detection method of the present invention, examples of another preferable detection means include an immunostaining method. The immunostaining method can be performed by the method well-known to a person skilled in the art.

A specific example of a preferable anti-GPC3 monoclonal antibody and anti-SPARC monoclonal antibody, which is used in the detection method of the present invention, is as described in the first aspect.

The detection method of the present invention can be used for obtaining an index for diagnosing whether a subject is affected with melanoma or not, and additionally, can be also performed with time for obtaining an index of the therapeutic effect on melanoma.

In a third aspect, the present invention provides an anti-GPC3 monoclonal antibody selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E; and an anti-SPARC monoclonal antibody selected from the group consisting of mAbS2F9, mAbS14A7, mAbS14C12, mAbS19B1, mAbS20D10, mAbS23C10, mAbS23E9 and mAbS25H9, the antibodies suitably used for the diagnostic kit of the first aspect and the detection method of the second aspect.

It is particularly preferred that the anti-GPC3 monoclonal antibody is selected from the group consisting of mAb2H10, mAb3E10, mAb3E11, mAbU3E and mAb3E3, and the anti-SPARC monoclonal antibody is selected from the group consisting of mAbS2F9, mAbS23C10, mAbS25H9 and mAbS23E9.

As described above, the anti-GPC3 monoclonal antibody and the anti-SPARC monoclonal antibody of the present invention include a fragment, and an altered antibody such as a chimeric antibody and a humanized antibody, as well as a variant antibody, of each of them. Examples of the fragment of an antibody include a $F(ab')_2$ fragment, and a Fab fragment. These fragment, altered antibody and variant antibody also have specificity for a GPC3 or SPARC protein, respectively, like the original anti-GPC3 monoclonal antibody or anti-SPARC monoclonal antibody. These can be produced by the means or method well-known to a person skilled in the art.

In a fourth aspect, the present invention provides a hybridoma selected from the group consisting of clone names 2C11, 2E11, 2H10, 3E3, 3E10, 3E11, 4F5, 5E5, 7C8, 7G6, 10A4 and U3E, which were deposited at NPMD under accession numbers NITE P-1326, NITE P-1327, NITE BP-01328, NITE P-1329, NITE BP-01330, NITE BP-01331, NITE P-1332, NITE P-1333, NITE P-1334, NITE P-1335, NITE P-1336 and NITE BP-01337, respectively; and a hybridoma selected from the group consisting of clone names S2F9, S14A7, S14C12, S19B1, S20D10, S23C10, S23E9 and S25H9, which were deposited at NPMD under accession numbers NITE BP-01338, NITE P-1339, NITE P-1340, NITE P-1341, NITE P-1342, NITE BP-01343, NITE P-1344 and NITE BP-01345, respectively, the hybridomas producing the monoclonal antibodies as defined in the third aspect.

Particularly preferably there are provided the hybridoma which is selected from the group consisting of clone names 2H10, 3E10, 3E11, U3E and 3E3; and the hybridoma which is selected from the group consisting of clone names S2F9, S23C10, S25H9 and S23E9.

The present invention will be further explained below by way of Examples, but the present invention is not limited by these Examples.

EXAMPLES

In the present invention, for the purpose of further improvement in sensitivity of a kit for diagnosing melanoma using the previously known anti-GPC3 antibody or anti-SPARC antibody, preparation of a novel monoclonal antibody was carried out. Specifically, as explained in detail below, 20 clones of hybridomas were established, and antibody purification was performed. Sandwich ELISA was constructed based on a purified antibody, and a verification experiment was performed using serum of Japanese melanoma patients (10 persons) and serum of Australian melanoma patients (10 persons). As a result, according to a combination of monoclonal antibodies used, the very high positive ratio of melanoma patients near 10% to 100% was attained.

Further, an additional verification experiment was carried out using serum of Japanese healthy subjects (100 persons), serum of Japanese patients of a dermatological disease other than melanoma (22 persons), serum of Japanese melanoma patients (56 persons), serum of Australian healthy subjects (11 persons), and serum of Australian melanoma patients (28 persons). In Japanese melanoma, diagnosis by means of a combination of GPC3 and SPARC of a novel method was more excellent than diagnosis by means of the previous tumor marker, LDH or 5-S-CD, in diagnosis of melanoma at a stage 0-3 in which there is no remote metastasis, particularly, in diagnosis at a stage 0-1 in which a possibility of complete cure is high. In addition, the diagnosis was shown to be also useful in differentiation from a patient of a dermatological disease other than melanoma. Also in Australian melanoma, it was shown that the positive ratio was as extremely high as the GPC3 positive ratio of 82.1%, and the SPARC positive ratio of 67.9%.

In Examples, the following abbreviations are used.

ABBREVIATIONS

GPC3: glypican-3
SPARC: secreted protein, acidic rich in cysteine
LDH; lactate dehydrogenase
5-S-CD: 5-S-cysteinyladopa
ALM: Acral lentiginous melanoma
SSM: Superficial spreading melanoma
LMM: Lentigo maligna melanoma
NN: nodular melanoma In addition, in Examples, "room temperature" means about 10 to 35° C.

Example 1

Method of Making Monoclonal Antibody

[1-1]
Preparation of Antigen

Ten μg of recombinant GPC3 (R & D Systems, GenBank ACCESSION NP_004475) or SPARC (Haematologic Technologies Inc., GenBank ACCESSION NM_003118) was prepared into 100 μL of PBS, and this was mixed with an artificial adjuvant TiterMax (registered trademark) (TiterMax USA Inc.) using an emulsion syringe to obtain an immunizing antigen.

[1-2]
Immunization of Mouse

A mixed emulsion of a GPC3 protein or a SPARC protein and an adjuvant was inoculated into a periphery of an inguinal region lymph node, an abdominal cavity, or a footpad of a BALB/c mouse. Frequent immunization with only a protein was performed three times every two weeks, and at the same time, a small amount of blood was collected from a tail vein, and the serum antibody titer was measured using ELISA. Three days before cell fusion, the mouse was finally immunized with 10 μg of a GPC3 protein or a SPARC protein. Each five BALB/c mice (8 week-old female, SPF bred) were used for making an anti-GPC3 antibody, or making an anti-SPARC antibody.

[1-3]
Measurement of the Serum Antibody Titer Using ELISA

After a GPC3 protein or a SPARC protein which had been adjusted at 0.1 μg/mL was immobilized on a 96 well ELISA plate (96 well Nunc Maxisorp plate (Nunc)), 4% Block Ace in PBS (DS Pharma Biomedical Co., Ltd.) was added at 200 μL/well to perform blocking. The plate was incubated at room temperature for 1 hour or longer, and washed using PBS-0.05% Tween 20 (PBST). Immunized mouse serum was diluted 100 to 10000 times, this was added to the ELISA plate at 50 μL/well, and the plate was incubated at room temperature for 2 hours. After washing with PBST, goat anti-mouse IgG(H+L) HRP-Conjugated (Jackson ImmunoResearch Laboratories, Inc.) was added, to perform incubation for 2 hours. After washing with PBST, water was sufficiently removed, and a TMB substrate was added at 50 μL/well to develop a color.

0.18 M sulfuric acid was overlaid to stop a coloring reaction. The absorbance at 450 nm was measured with a plate reader (Bio-Rad, model 550) to conduct analysis.

A mouse in which increase in the serum antibody titer had been confirmed by ELISA was used in cell fusion.

[1-4]
Cell Fusion

In the present step, four kinds of conditioned media constructed of the following composition were used depending on an object:

1) Serum-free medium; RPMI1640 (Sigma)+penicillin-streptomycin-glutamine,
2) HAT-selective medium; HAT (hypoxanthine/thymidine/aminopterin)+10% fetal bovine serum+penicillin-streptomycin-glutamine+BM condimed H1 (Roche)+RPMI1640,
3) HT-selective medium; HT (hypoxanthine/thymidine)+10% fetal bovine serum+penicillin-streptomycin-glutamine+BM-condimed H1 (Roche)+RPMI1640,
4) Hybridoma culturing medium; 10% fetal bovine serum+penicillin-streptomycin-glutamine+BM-condimed MEM+NAEE+sodium pyruvate solution+RPMI1640.

In addition, these medium components will be explained in detail below.

HAT (Invitrogen), trade name: HAT Supplement (50×), composition; 5 mM hypoxanthine sodium salt, 20 μM thymidine, 0.8 mM aminopterin; use at 50-fold dilution.

HT (Invitrogen), trade name: HT Supplement (100×), composition; 10 mM hypoxanthine sodium salt, 1.6 mM thymidine; use at 100-fold dilution.

BM condimed H1 (Roche); published main composition; supernatant of PMA-stimulated mouse lymphoma cell line, and 1 mM oxaloacetic acid, 200 NM insulin, 1 ng/ml hIL-6, 10 nM PMA, 15% FBS; use by addition to final concentration of 10%.

Penicillin-streptomycin-glutamine (Invitrogen), trade name; Penicillin-Streptomycin-Glutamine (100×), concentration; 10,000 unit/ml penicillin, 10,000 μg/ml streptomycin, 29.2 mg/ml L-glutamine; use at 100-fold dilution.

NEAA (Invitrogen), trade name; MEM Non-Essential Amino Acid Solution (100×), composition; 10 mM glycine, 10 mM L-alanine, 10 mM L-asparagine, 10 mM L-aspartic acid, 10 mM glutamic acid, 10 mM L-proline, 10 mM L-serine; use at 100-fold dilution.

Sodium pyruvate solution (Invitrogen), trade name; Sodium Pyruvate Solution 100 mM (100×), concentration 100 mM; use at 100-fold dilution.

Within 3 days after final immunization of a BALB/c mouse, a spleen was collected, and homogenized with a rough surface of a frost glass slide, and a cell suspension was filtered with a nylon mesh.

A centrifugation-washed spleen cell was re-suspended in 20 mL of a serum-free medium, and the total cell number was counted with a hemocytometer. A myeloma cell strain Sp2/O—Ag. 14 (mouse myeloma cell strain Sp2/O—Ag. 14 was obtained from RIKEN Cell Bank.) which is a spleen fusion partner was centrifugation-washed, and suspended in a serum-free medium, and the cell number was counted.

A spleen cell and a myeloma were mixed at the cell ratio of 5:1, and this was centrifugation-washed. One mL of a 50% PEG 1500 solution (retained at a temperature of 37° C.) was slowly added to a cell mixed pellet over 2 minutes, while stirring with a pipette.

One mL of a serum-free medium (retained at a temperature of 37° C.) was slowly added two times over 1 minute, while stirring. Further, 7 mL of a serum-free medium (37° C.) was slowly added over 3 minutes, while stirring. A cell suspension after completion of fusion operation was centrifugation-washed at room temperature and 1,000 rpm for 5 minutes. A spleen cell was suspended in a hybridoma culturing medium so that the cell number became $2.5\times10^5$ cells/100 μL, and the cell suspension at 100 μL per one well was added to a 96 well culturing plate. The cell was cultured in a 5% $CO_2$ incubator at 37° C. After culturing for 18 hours, a HAT selective medium was added to culture the cell for 2 weeks.

[1-5]

Selective Culturing and Screening of a Fused Cell

After selective culturing for 2 weeks, a living cell (cell fusion-positive colony) was observed under a microscope, 100 μL of the culturing supernatant of the positive colony was recovered, and ELISA was performed by immobilization of an antigen. When the number of positive colonies was large, and it was difficult to separately recover the culturing supernatant, sampling of the culturing supernatant was performed by applying experimental design (for details, "Introduction of Monoclonal Antibody Experimental Procedure" (published in 1991)", Tamie Ando, Joe Chiba, Kodansha Scientific Ltd.).

[1-6]

Screening Method by ELISA

An experimental procedural method was performed by the same procedure as that of the "measurement of the serum antibody titer using ELISA" described in [1-3]. The culturing supernatant was used as an undiluted solution.

[1-7]

Cloning of Hybridoma

A hybridoma, for which antibody production had been confirmed, was transferred from a 96 well plate to a 24 well culturing plate, and cultured on a selective medium until the cell became semiconfluent. In order to acclimate to HT, the cell was transferred to a HT selective medium to acclimate to a HT selective medium. A fused cell which had been cultured in 24 wells was cultured until semiconfluent. When the cell became to sufficiently proliferate in a HT medium, the cell was transferred from the 24 wells to a 6-well culturing plate, that is, transferred to a hybridoma culturing medium to conduct acclimation for about 7 days. After a hybridoma was cultured until stable proliferation on normal RPMI1640, clones which proliferate rapidly and have a large antibody production amount were cloned using a limiting dilution method.

The results of ELISA of an anti-SPARC monoclonal antibody which was selected, cloned, and produced from a hybridoma are shown in FIG. 1. Similarly, the results of ELISA of an anti-GPC3 monoclonal antibody which was selected, cloned, and produced from a hybridoma are shown in FIG. 2.

2C11, 2E11, 2H10, 3E3, 3E10, 3E11, 4F5, 5E5, 7C8, 7G6, 10A4 and U3E which are clones having the high anti-GPC3 antibody producing ability among the resulting clones of hybridomas were deposited at National Institute of Technology and Evaluation (NITE), NITE Patent Microorganisms Depositary (NPMD) under accession numbers NITE P-1326, NITE P-1327, NITE BP-01328, NITE P-1329, NITE BP-01330, NITE BP-01331, NITE P-1332, NITE P-1333, NITE P-1334, NITE P-1335, NITE P-1336 and NITE BP-01337, respectively. For details of deposition, see the paragraph following the header "Explanation of deposition" above and Table 10.

In addition, S2F9, S14A7, S14C12, S19B1, S20D10, S23C10, S23E9 and S25H9 which are clones having the high anti-SPARC antibody producing ability among the resulting clones of hybridomas were deposited at National Institute of Technology and Evaluation (NITE), NITE Patent Microorganisms Depositary (NPMD) under accession numbers NITE BP-01338, NITE P-1339, NITE P-1340, NITE P-1341, NITE P-1342, NITE BP-01343, NITE P-1344 and NITE BP-01345, respectively. For details of deposition, see the paragraph following the header "Explanation of deposition" above and Table 10.

[1-8]

Method of Purifying Antibody

A monoclonal antibody was purified from ascites obtained a few weeks after inoculation of a hybridoma producing an intended antibody into an abdominal cavity of a BALB/c or nude mouse, or the culturing supernatant obtained by culturing a hybridoma producing an intended antibody.

Preparation of Ascites

A BALB/c mouse (9 to 10 weeks old) was irradiated with an X ray at 3.5 Gy, 0.2 ml of pristane was injected into an abdominal cavity after 3 days, and the mouse was reared for 7 to 10 days. A hybridoma which had been increased by culturing was recovered, and centrifugation-washed with 5 ml of a serum-free medium two times. A cell suspension was prepared with RPMI, and $1\times10^6$ cells were inoculated into an abdominal cavity of a mouse. After 7 to 10 days, a 18 G injection needle was pinpricked into an abdominal cavity to recover ascites into a centrifuging tube. Ascites was centrifuged at 1200 rpm for 5 minutes to separate an erythrocyte. The supernatant was collected, and frozen and stored at −20° C. until operation of antibody purification.

Purification of Antibody from Ascites or Culturing Supernatant of Hybridoma (Affinity Purification of Antibody)

Purification of an antibody was performed by affinity purification using Protein A-conjugated Sepharose (GE Healthcare) or Protein G-conjugated Sepharose (GE Healthcare). Alternatively, an antibody can also be purified using an antigen column made by immobilizing GPC3 or SPARC on a ligand coupling carrier, such as CNBr-activated Sepharose 4B (GE Healthcare).

Specifically, for purifying an antibody from ascites, ascites was diluted with PBS appropriately (to a degree of 1/2 to 1/5), and purified by Protein A-Sepharose. As a washing buffer, PBS was used, and as an elution buffer, 0.1 M glycine-HCl pH 2.8 was used.

For purifying an antibody from the culturing supernatant of a hybridoma, a medium in which a hybridoma had been cultured at a large scale of 250 mL to 1 L was recovered, and filtered with a 0.2 micron filter in order to prevent deterioration of a column. The medium was flown through a column filled with Protein A to adsorb an antibody thereon. After washing with a 10-fold column volume or more of PBS, an antibody was acid-eluted using 0.1 M glycine-HCl pH 2.7, and 1 M Tris-HCl pH 8 was immediately added to an eluate to neutralize the pH.

Example 2

Study of Combination of Appropriate Antibodies (Capture Antibody/Detection Antibody) for Sandwich ELISA

[2-1]

Sandwich ELISA of GPC3

A capture antibody (one kind among anti-GPC3 antibodies) was adjusted with PBS, pH 7.4 to 1 μg/mL, 50 μL per one well was coated on a 96 well Nunc Maxisorp ELISA plate (Nunc), and this was incubated at room temperature for 1 hour or longer. Blocking was performed at room temperature for 1 hour using 4% Block Ace (DS Pharma BIOMEDICAL Co., Ltd.) (4 g/100 mL PBS) or 1% BSA (1 g BSA/100 mL PBS). A specimen sample obtained by diluting patient plasma or serum with 0.4% Block Ace (DS Pharma Biomedical Co., Ltd.) three or more times, or an undiluted solution of the culturing supernatant of a melanoma cell was added at 50 μL per one well, and this was incubated at room temperature for 2 hours. After this was washed three times with PBS (PBST) with 0.05% Tween 20 added thereto, 50 μL of a 1 μg/mL biotinylated detection antibody (one kind among anti-GPC3 antibodies) which had been adjusted with 4% Block Ace was added, and this was incubated at room temperature for 1 hour. Biotinylation of an antibody was performed using EZ-link NHS-Biotin reagent (Thermo Scientific). After washing with PBST three times, 1 mg/mL horseradish peroxidase-conjugated streptavidin which had been diluted 5000 times with 0.4% Block Ace was added at 50 μL per each well, and this was incubated at room temperature for 30 minutes. After washing with PBST three times, a TMB substrate solution (Thermo Scientific) was added to develop a color, and 50 μL of 0.18 M sulfuric acid was added to stop a coloring reaction. The absorbance at 450 nm was measured with a plate reader (Bio-Rad, model 550), and analysis was performed.

The results of sandwich ELISA of GPC3 are shown in FIG. 3 and Table 1. As a capture antibody for GPC3, mAb2C11, mAb10A4, mAbU3E and mAb3E11 were excellent, and as a detection antibody, mAb2H10, mAb3E10, and mAb3E3 were excellent.

Figure 5:
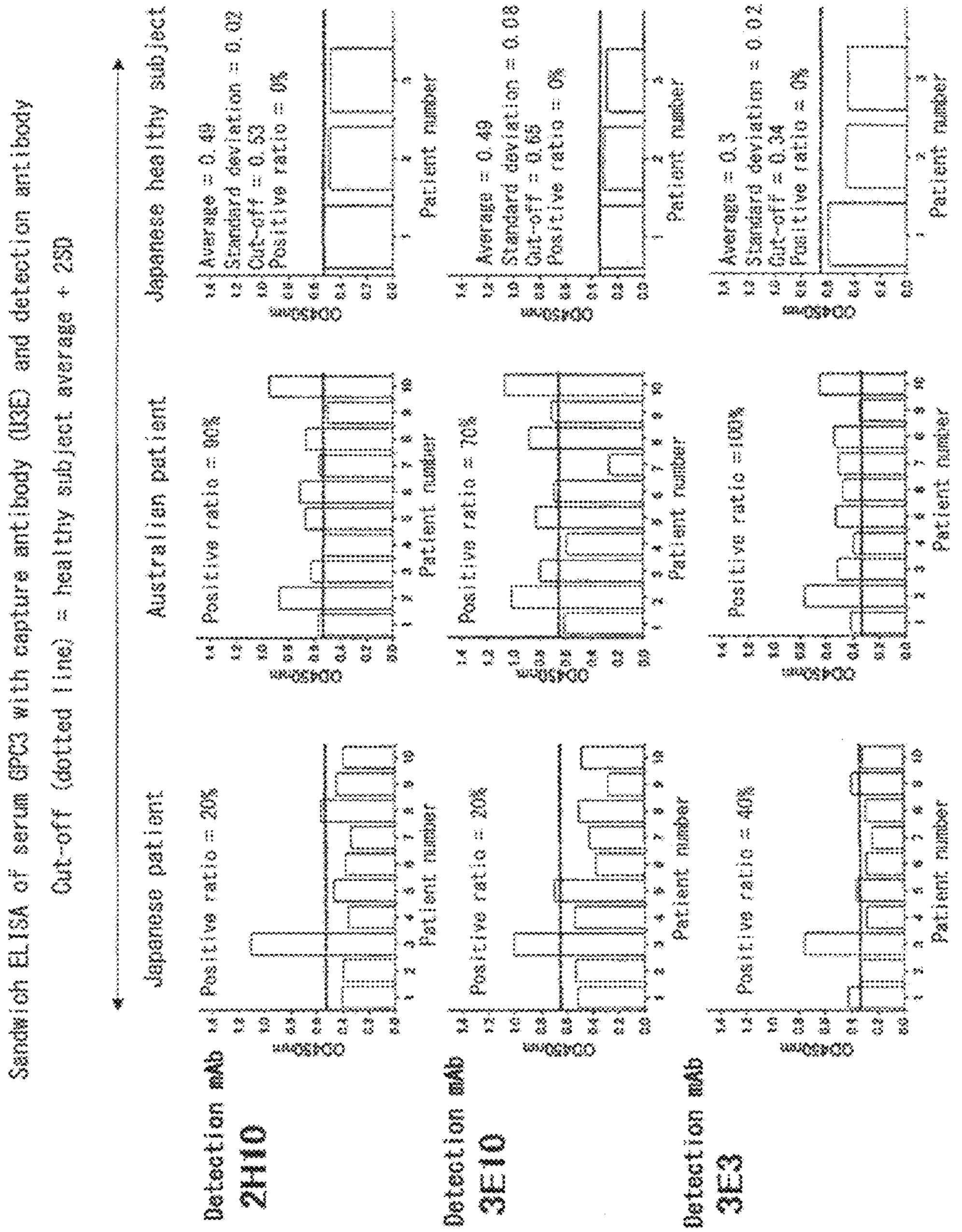
FIG. 5 shows the result of sandwich ELISA of serum GPC3 when mAbU3E is used as a capture antibody.

In addition, a capture antibody was immobilized on mAbU3E, and detection of a Japanese or Australian melanoma patient sample was performed using any of mAb2H10, mAb3E10, and mAb3E3 as a detection antibody. The results are shown in FIG. 5 and on the left side of Table 3. The positive ratio of Australian melanoma in the case where mAbU3E and mAb3E3 were used in combination was 100%. In addition, for a healthy subject, the positive ratio was 0%, and specificity was high, in all cases.

[2-2]

Sandwich ELISA of SPARC

In sandwich ELISA using an anti-SPARC antibody, SPARC was detected from melanoma patient blood/plasma or the melanoma cell culturing supernatant by sandwich ELISA under the same condition as that of the anti-GPC3 antibody.

Figure 4:
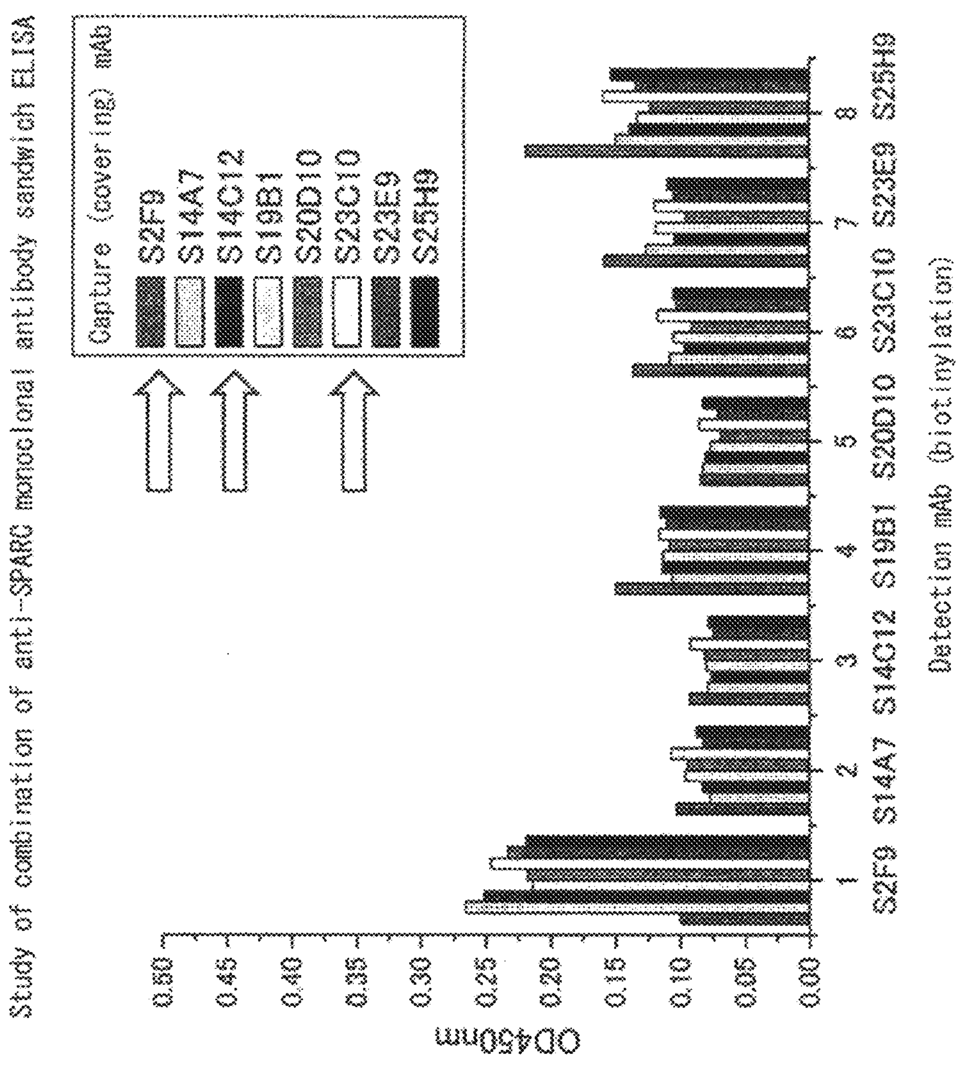
FIG. 4 shows the result of study of a combination of antibodies for sandwich ELISA concerning an anti-SPARC monoclonal antibody.

The results of sandwich ELISA of SPARC are shown in FIG. 4 and Table 2. As a capture antibody for SPARC, mAbS2F9, mAbS14C12 and mAbS23C10 were excellent, and as a detection antibody, mAbS2F9, mAbS25H9, mAbS23E9 and mAbS23C10 were excellent.

In addition, a capture antibody was immobilized on mAbS23C10, and detection of a Japanese or Australian melanoma patient sample was performed using any of mAbS2F9, mAbS25H9 and mAbS23E9 as a detection antibody. The results are shown in FIG. 6 and on the right side of Table 3. The positive ratio of Australian melanoma in the case where mAbS23C10 and mAbS2F9 or mAbS25H9 were used in combination was 100%. In addition, for a healthy subject, the positive ratio was 0%, and specificity was high, in all cases.

[2-3]

Combination of Sandwich ELISA of GPC3 and Sandwich ELISA of SPARC

Sandwich ELISA of GPC3 and sandwich ELISA of SPARC of [2-1] and [2-2] were combined, and detection was performed using samples of a Japanese melanoma patient, an Australian melanoma patient, and a Japanese healthy subject.

As a capture antibody for GPC3, mAbU3E was used, and as a detection antibody, any of mAb2H10, mAb3E10 and mAb3E3 was used.

On the other hand, as a capture antibody for SPARC, mAbS23C10 was used, and as a detection antibody, any of mAbS2F9, mAbS25H9 and mAbS23E9 was used.

The results are shown in Tables 4 to 6. In the case where sandwich ELISA of GPC3 and sandwich ELISA of SPARC were combined, the positive ratio of an Australian melanoma patient was as very high as 90 to 100%, and the positive ratio of a Japanese melanoma patient was also as relatively high as 30 to 80%. In addition, for a Japanese healthy subject, the positive ratio was 0%, and specificity was high, in all cases.

TABLE 1

Condition of combination of sandwich ELISA of an anti-GPC3 monoclonal antibody

| | | Capture mAb (which covers a plate) | | | | | | | | | | | |
|---|---|---|---|---|---|---|---|---|---|---|---|---|---|
| | | 2C11 | 2E11 | 2H10 | 3E3 | 3E10 | 3E11 | 4F5 | 5E5 | 7C8 | 7G6 | 10A4 | U3E |
| Detection mAb | 2C11 | 0.005 | 0.016 | 0.008 | −1.00E−03 | −0.002 | −0.013 | −0.003 | 0.006 | −0.003 | −0.014 | −0.012 | −0.004 |
| | 2E11 | 0.07 | 0.053 | 0.042 | 0.032 | 0.038 | 0.024 | 0.04 | 0.061 | 0.044 | 0.045 | 0.049 | 0.062 |
| | 2H10 | 0.458 | 0.321 | 0.258 | 0.292 | 0.301 | 0.347 | 0.397 | 0.397 | 0.409 | 0.422 | 0.519 | 0.562 |
| | 3E3 | 0.18 | 0.163 | 0.125 | 0.134 | 0.114 | 0.122 | 0.138 | 0.17 | 0.149 | 0.167 | 0.16 | 0.195 |
| | 3E10 | 0.305 | 0.263 | 0.222 | 0.283 | 0.248 | 0.28 | 0.302 | 0.312 | 0.317 | 0.332 | 0.347 | 0.442 |

TABLE 1-continued

| Condition of combination of sandwich ELISA of an anti-GPC3 monoclonal antibody Capture mAb (which covers a plate) | | | | | | | | | | | | | |
|---|---|---|---|---|---|---|---|---|---|---|---|---|---|
| | | 2C11 | 2E11 | 2H10 | 3E3 | 3E10 | 3E11 | 4F5 | 5E5 | 7C8 | 7G6 | 10A4 | U3E |
| | 3E11 | 0.091 | 0.075 | 0.052 | 0.043 | 0.026 | 0.037 | 0.033 | 0.051 | 0.041 | 0.039 | 0.05 | 0.054 |
| | 4F5 | 0.063 | 0.05 | 0.035 | 0.025 | 0.007 | 0.003 | −0.002 | 0.022 | −0.002 | 0.005 | −0.002 | 0.021 |
| | 5E5 | 0.121 | 0.108 | 0.105 | 0.091 | 0.059 | 0.053 | 0.051 | 0.088 | 0.058 | 0.071 | 0.059 | 0.084 |
| | 7C8 | 0.074 | 0.065 | 0.068 | 0.062 | 0.064 | 0.062 | 0.063 | 0.068 | 0.07 | 0.06 | 0.068 | 0.061 |
| | 7G6 | 0.01 | 0.01 | 0.02 | 0.018 | 0.016 | 0.03 | 0.02 | 0.1 | 0.02 | 0.02 | 0.017 | 0.18 |
| | 10A4 | 0.127 | 0.105 | 0.088 | 0.088 | 0.087 | 0.091 | 0.107 | 0.113 | 0.109 | 0.1 | 0.104 | 0.108 |
| | U3E | 0.08 | 0.083 | 0.079 | 0.081 | 0.077 | 0.075 | 0.076 | 0.09 | 0.085 | 0.077 | 0.076 | 0.084 |

TABLE 2

| Condition of combination of sandwich ELISA of an anti-SPARC monoclonal antibody Capture mAb (which covers a plate) | | | | | | | | | |
|---|---|---|---|---|---|---|---|---|---|
| | | S2F9 | S14A7 | S14C12 | S19B1 | S20D10 | S23C10 | S23E9 | S25H9 |
| Detection mAb | S2F9 | 0.1 | 0.266 | 0.252 | 0.214 | 0.218 | 0.246 | 0.233 | 0.219 |
| | S14A7 | 0.103 | 0.077 | 0.083 | 0.096 | 0.094 | 0.107 | 0.082 | 0.087 |
| | S14C12 | 0.093 | 0.079 | 0.076 | 0.08 | 0.081 | 0.092 | 0.074 | 0.078 |
| | S19B1 | 0.149 | 0.106 | 0.113 | 0.113 | 0.108 | 0.116 | 0.111 | 0.115 |
| | S20D10 | 0.084 | 0.082 | 0.08 | 0.076 | 0.068 | 0.085 | 0.071 | 0.082 |
| | S23C10 | 0.136 | 0.108 | 0.097 | 0.105 | 0.091 | 0.117 | 0.103 | 0.105 |
| | S23E9 | 0.158 | 0.126 | 0.104 | 0.119 | 0.096 | 0.12 | 0.105 | 0.11 |
| | S25H9 | 0.219 | 0.15 | 0.139 | 0.133 | 0.123 | 0.159 | 0.134 | 0.153 |

Table 3 is a table summarizing the results of sandwich ELISA concerning GPC3 or SPARC.

TABLE 3

| Sandwich ELISA | | | |
|---|---|---|---|
| GPC3 U3E capture Ab/2H10 detection Ab | | SPARC S23C10 capture Ab/S2F9 detection Ab | |
| Patient (number) | GPC3 positive ratio Healthy subject average + 2SD = 0.53 | Patient (number) | SPARC positive ratio Healthy subject average + 2SD = 0.18 |
| Japanese patient (10) | 20% | Japanese patient (10) | 80% |
| Australian patient (10) | 90% | Australian patient (10) | 100% |
| Japanese healthy subject (3) | 0% | Japanese healthy subject (3) | 0% |
| U3E capture Ab/3E10 detection Ab | | S23C10 capture Ab/S25H9 detection Ab | |
| Patient (number) | GPC3 positive ratio Healthy subject average + 2SD = 0.65 | Patient (number) | SPARC positive ratio Healthy subject average + 2SD = 0.15 |
| Japanese patient (10) | 20% | Japanese patient (10) | 70% |
| Australian patient (10) | 70% | Australian patient (10) | 100% |
| Japanese healthy subject (3) | 0% | Japanese healthy subject (3) | 0% |
| U3E capture Ab/3E3 detection Ab | | S23C10 capture Ab/S23E9 detection Ab | |
| Patient (number) | GPC3 positive ratio Healthy subject average + 2SD = 0.34 | Patient (number) | SPARC positive ratio Healthy subject average + 2SD = 0.25 |
| Japanese patient (10) | 40% | Japanese patient (10) | 10% |
| Australian patient (10) | 100% | Australian patient (10) | 80% |
| Japanese healthy subject (3) | 0% | Japanese healthy subject (3) | 0% |

Tables 4 to 6 are tables summarizing the results of the cases where sandwich ELISAs concerning GPC3 and SPARC are combined.

TABLE 4

| Positive ratio by combination of GPC3 and SPARC sandwich ELISAs 1 | | | |
|---|---|---|---|
| Patient (number) | GPC3 positive ratio Healthy subject average + 2SD = 0.53 | SPARC positive ratio Healthy subject average + 2SD = 0.18 | GPC3 positive ratio/SPARC positive ratio |
| U3E capture Ab/2H10 detection Ab S23C10 capture Ab/S2F9 detection Ab | | | |
| Japanese patient (10) | 20% | 80% | 80% |
| Australian patient (10) | 90% | 100% | 100% |
| Japanese healthy subject (3) | 0% | 0% | 0% |
| U3E capture Ab/2H10 detection Ab S23C10 capture Ab/S25H9 detection Ab | | | |
| Japanese patient (10) | 20% | 70% | 70% |
| Australian patient (10) | 90% | 100% | 100% |
| Japanese healthy subject (3) | 0% | 0% | 0% |
| U3E capture Ab/2H10 detection Ab S23C10 capture Ab/S23E9 detection Ab | | | |
| Japanese patient (10) | 20% | 10% | 30% |
| Australian patient (10) | 90% | 80% | 100% |
| Japanese healthy subject (3) | 0% | 0% | 0% |

TABLE 5

| Positive ratio by combination of GPC3 and SPARC sandwich ELISAs 2 | | | |
|---|---|---|---|
| Patient (number) | GPC3 positive ratio Healthy subject average + 2SD = 0.53 | SPARC positive ratio Healthy subject average + 2SD = 0.18 | GPC3 positive ratio/SPARC positive ratio |
| U3E capture Ab/3E10 detection Ab S23C10 capture Ab/S2F9 detection Ab | | | |
| Japanese patient (10) | 20% | 70% | 80% |
| Australian patient (10) | 70% | 100% | 100% |
| Japanese healthy subject (3) | 0% | 0% | 0% |
| U3E capture Ab/3E10 detection Ab S23C10 capture Ab/S25H9 detection Ab | | | |
| Japanese patient (10) | 20% | 70% | 80% |
| Australian patient (10) | 70% | 100% | 100% |
| Japanese healthy subject (3) | 0% | 0% | 0% |

TABLE 5-continued

| Positive ratio by combination of GPC3 and SPARC sandwich ELISAs 2 | | | |
|---|---|---|---|
| Patient (number) | GPC3 positive ratio Healthy subject average + 2SD = 0.53 | SPARC positive ratio Healthy subject average + 2SD = 0.18 | GPC3 positive ratio/SPARC positive ratio |
| U3E capture Ab/3E10 detection Ab S23C10 capture Ab/S23E9 detection Ab | | | |
| Japanese patient (10) | 20% | 10% | 30% |
| Australian patient (10) | 70% | 80% | 90% |
| Japanese healthy subject (3) | 0% | 0% | 0% |

TABLE 6

| Positive ratio by combination of GPC3 and SPARC sandwich ELISAs 3 | | | |
|---|---|---|---|
| Patient (number) | GPC3 positive ratio Healthy subject average + 2SD = 0.53 | SPARC positive ratio Healthy subject average + 2SD = 0.18 | GPC3 positive ratio/SPARC positive ratio |
| U3E capture Ab/3E3 detection Ab S23C10 capture Ab/S2F9 detection Ab | | | |
| Japanese patient (10) | 40% | 80% | 80% |
| Australian patient (10) | 100% | 100% | 100% |
| Japanese healthy subject (3) | 0% | 0% | 0% |
| U3E capture Ab/3E3 detection Ab S23C10 capture Ab/S25H9 detection Ab | | | |
| Japanese patient (10) | 40% | 70% | 80% |
| Australian patient (10) | 100% | 100% | 100% |
| Japanese healthy subject (3) | 0% | 0% | 0% |
| U3E capture Ab/3E3 detection Ab S23C10 capture Ab/S23E9 detection Ab | | | |
| Japanese patient (10) | 40% | 10% | 40% |
| Australian patient (10) | 100% | 80% | 100% |
| Japanese healthy subject (3) | 0% | 0% | 0% |

Example 3

Method

[3-1]

Specimen of Healthy Subject Comparative Control Group

As a Japanese healthy subject specimen, an excessive specimen obtained by collecting blood in health examination/encounter was used. Sera of 100 specimens in which breakdown of clinical setting was such that there was no anamnesis of cancer, diabetes and glaucoma, an average age was 50.2 years old, and the ratio of men to women was 50/50 were used. In Australian healthy subjects, sera in which the ratio of men to women was 3/8, and an average age was 56.0 years old were used.

[3-2]

Specimen of Melanoma Patient and Patient of Dermatological Disease Other than Melanoma In Japanese melanoma patients, sera in which the number of patients whose disease type or disease stage had been confirmed was 56, the ratio of men to women was 26/30, and an average age was 64.1 years old were used. In 22 patients of a dermatological disease other than melanoma, sera in which the ratio of men to women was 11/11, and an average age was 60.55 years old were used. In 28 Australian melanoma patients, sera in which the ratio of men to women was 20/8, and an average age was 56.3 years old were used.

[3-3]

Preparation of Anti-GPC3 Monoclonal Antibody and Anti-SPARC Monoclonal Antibody

Seven days before hybridoma inoculation, a BALB/c mouse was exposed to radiation at 3.5 Gy, and pristane was inoculated into its abdominal cavity after 3 days. $1\times10^5$ or more hybridomas were inoculated, and ascites was recovered after 1 to 2 weeks. Recovered ascites was centrifuged (15000 rpm/30 min) to remove insoluble particles, and this was filter-filtrated using a syringe filter having a 0.45 μm pore size (Nunc). In order to purify an antibody from ascites, affinity chromatography using a column filled with Protein G Sepharose (GE Healthcare) was performed. Ascites was diluted with PBS five times, and flown through a Protein G column to adsorb an antibody thereon. In order to remove non-specifically adsorbed debris, the column was washed with PBS, and an antibody was acid-eluted using 0.1 M glycine-HCl pH 2.7. The eluted antibody was instantaneously mixed with 1 M Tris-HCl pH 8.0 to adjust the pH at around neutral. The concentration of the purified antibody was calculated from a measured value of ultraviolet absorption at 280 nm and a molecular extinction coefficient of 1.4.

[3-4]

Biotinylation of Antibody

An antibody was biotinylated using a NHS-LC-Biotinylation reagent (Pierce) and a NHS-LC-LC-Biotinylation reagent (Pierce) according to the protocol of the manufacturer.

[3-5]

Sandwich ELISA

[3-5-1]

Sandwich ELISA of GPC3 with Novel Antibody

In sandwich ELISA for detecting GPC3, each of capture antibodies mAbU3E and mAb3E11 was adjusted to 5 μg/mL, and 50 μL was added per one well of a 96 well Maxisorp plate to adsorb the antibody thereon. In order to prevent non-specific adsorption, blocking was performed with 1 to 2% Block Ace (DS Pharma Biomedical Co., Ltd.). 50 μL of a measurement serum sample which had been diluted with 0.1% Block Ace 2 to 4 times was added to an ELISA plate coated with a capture antibody, and this was incubated at 4° C. for 12 hours or longer. After washing with PBS containing 0.05% Tween 20, a biotin-labeled detection antibody cocktail (containing mAb2H10, mAb3E3, and mAb3E10) was added at 50 μL per one well, and this was incubated at room temperature for 2 hours or longer. After washing with PBS containing 0.05% Tween 20, avidin-horseradish peroxidase was added, this was incubated at room temperature for 30 minutes, and thereafter, this was washed with PBS containing 0.05% Tween 20. After a TMB substrate solution was added to develop a color, and sufficiently perform a coloring reaction, 50 μL of 0.18 M sulfuric acid was added to stop the reaction. The absorbance at 450 nm was measured and quantitated using Multiplate reader (BioRad).

[3-5-2]

Sandwich ELISA of GPC3 with Commercially Available Antibody

As a capture antibody, an anti-human GPC3 monoclonal antibody 1G12 (Biomosic) was used, and as a detection antibody, an anti-GPC3 polyclonal antibody (#A2119, R&D Systems) was used. An experimental operation of ELISA was performed according to the same manner as that of the novel method.

[3-5-3]

Sandwich ELISA of SPARC with Novel Antibody

As a capture antibody, mAbS2F9 was used, and as a detection antibody, a detection antibody cocktail containing biotinylated mAbS23C10, mAbS23E9 and mAbS25H9 was used. An experimental procedure of ELISA was performed as in the case of GPC3.

Result

[3-A] Result of Study Using Japanese Specimen

[3-A-1]

Figure 7:
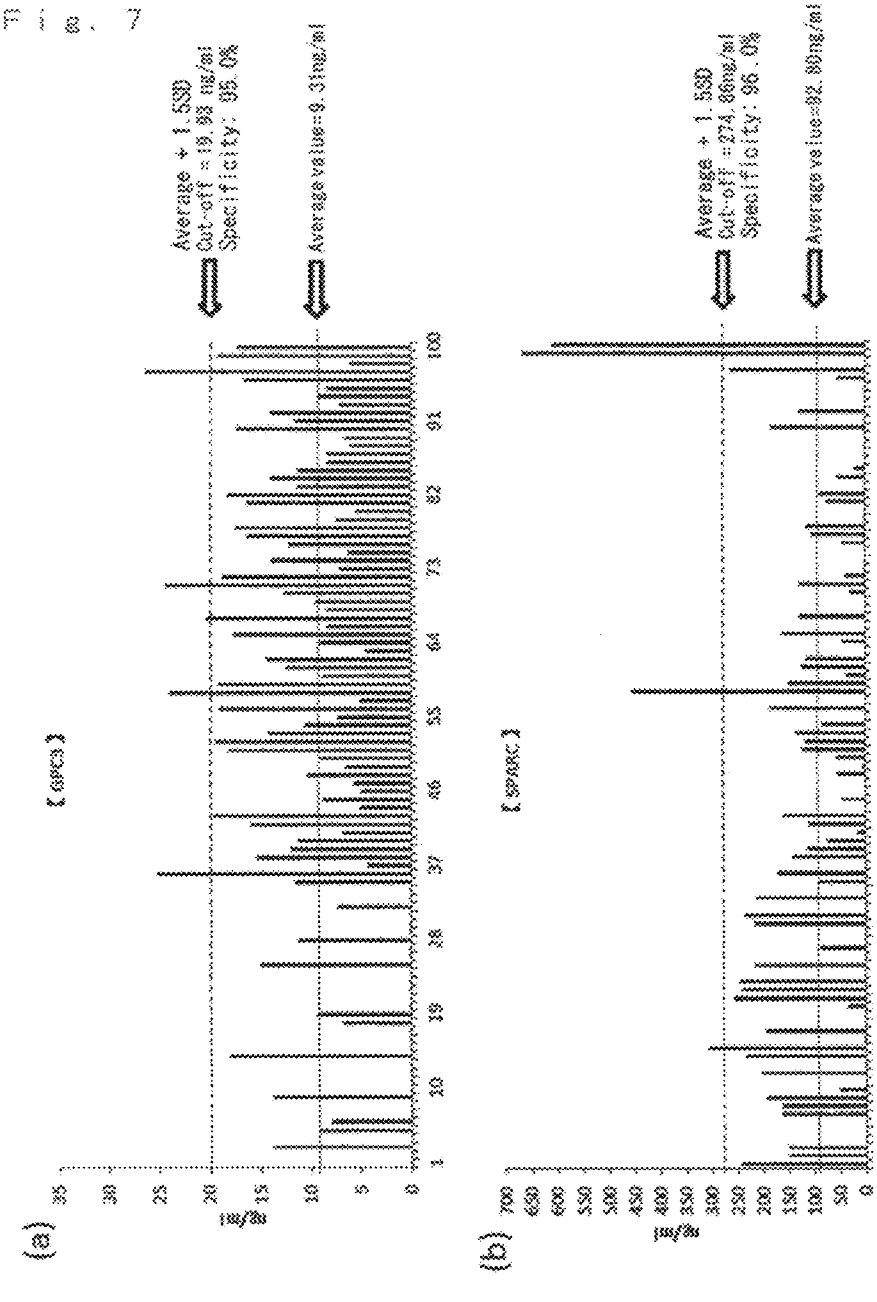
FIG. 7 shows setting of cut-off by serum GPC3 (a) and SPARC (b) values of 100 Japanese healthy subjects using sandwich ELISA using a novel antibody.

Setting of Cut-Off by Serum GPC3 and SPARC Values of 100 Japanese Healthy Subjects Using Sandwich ELISA Using Novel Antibody (FIG. 7)

In order to determine cut-off of GPC3 and SPARC in ELISA using a novel antibody, ELISA of sera of 100 Japanese healthy subjects was performed (FIG. 7). The results of quantitation of GPC3 are shown in FIG. 7 (*a*), and the results of quantitation of SPARC are shown in FIG. 7 (*b*). A cut-off value was calculated from a concentration average value in sera of GPC3 and SPARC of 100 healthy subjects, and a standard deviation. The determined cut-off value is shown on the graph with a dotted line.

[3-A-2]

Cut-Off of Japanese Healthy Subject in Sandwich ELISA Using Novel Antibody (Table 7)

Sera of healthy subjects in which breakdown of a comparative control group (healthy subject) relative to a melanoma patient was such that an average age was 50.2 years old, the ratio of men to women was 50/50, and there was no anamnesis of a cancer/lifestyle disease were selected for measurement. When cut-off determined from healthy subjects was expressed as average+1.5×SD, cut-off of GPC3 was 19.93 ng/mL, specificity was 95%, and as a false positive case, five cases were seen (FIG. 7 (*a*)). In SPARC, cut-off was 274 ng/mL, specificity was 96%, and four cases of false positive were seen (FIG. 7 (*b*)).

TABLE 7

Cut-off of Japanese healthy subject in sandwich ELISA using novel antibody

| | | (ng/ml) | Positive subject | Specificity |
|---|---|---|---|---|
| GPC3 | Average + SD | 16.391 | 19 | 81% |
| | Average + 1.5SD | 19.930 | 5 | 95% |
| | Average + 2SD | 23.468 | 4 | 96% |
| SPARC | Average + SD | 214.173 | 13 | 87% |
| | Average + 1.5SD | 274.860 | 4 | 96% |
| | Average + 2SD | 335.547 | 3 | 97% |

n = 100: age = 50.2 ± 6.7

[3-A-3]

GPC3 and SPARC Values of 22 Cases of Japanese Patients of Dermatological Disease Other than Melanoma (FIG. 8)

Regarding serum GPC3 and SPARC of a dermatological disease other than melanoma, ELISA using a novel antibody was performed, and the results are shown in FIG. 8. In both of GPC3 and SPARC, when cut-off determined from measurement of GPC3 and SPARC of a healthy subject was applied, no case of positive determination was seen (FIGS. 8 (*a*) and (*b*)). Therefore, from these results, it was shown that differential diagnosis between melanoma and other dermatological disease can be performed.

[3-A-4]

Figure 9:
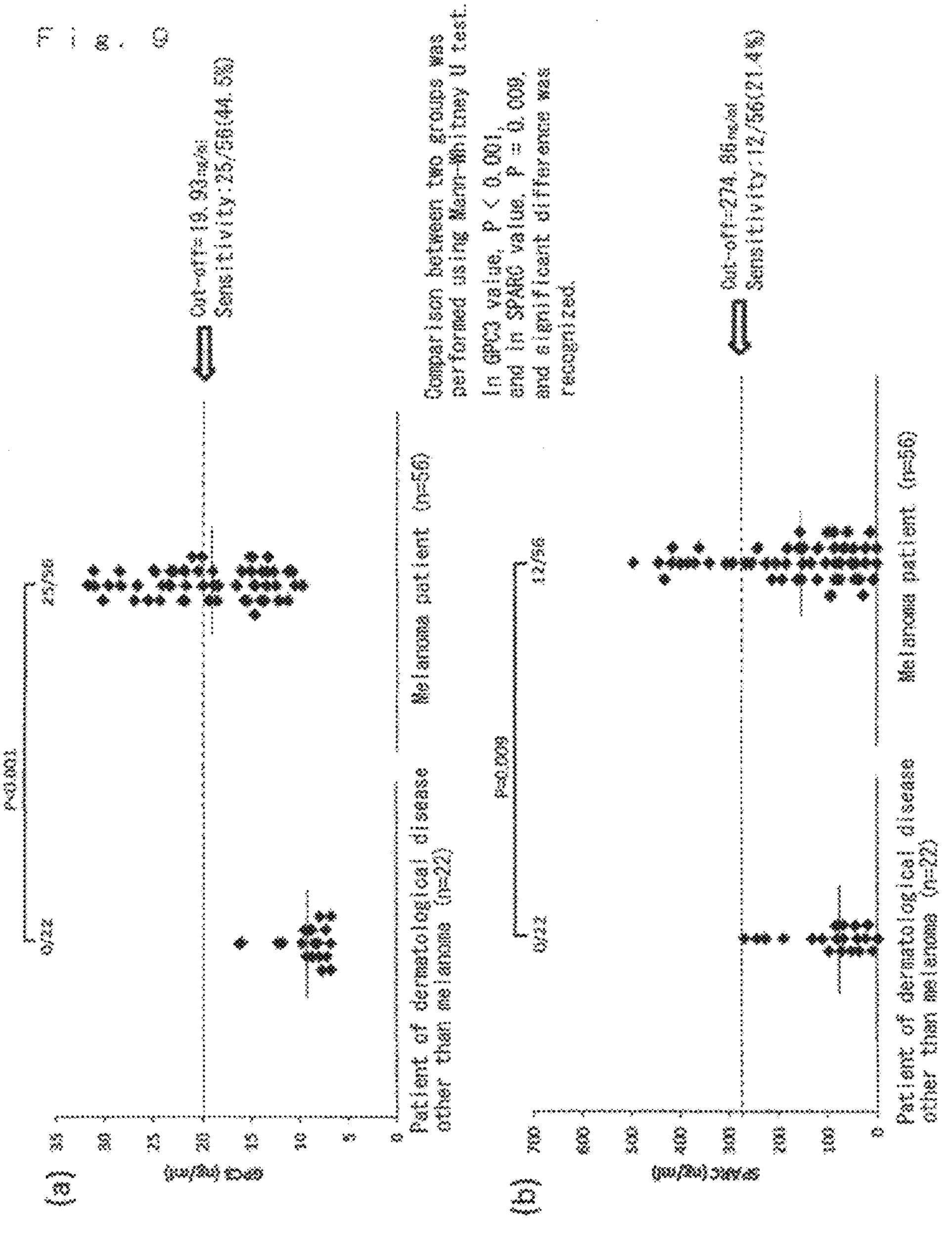
FIG. 9 shows distributions of GPC3 values (a) and SPARC values (b) of Japanese patients of a dermatological disease other than melanoma (n=22) and Japanese melanoma patients (n–56).

Distribution of GPC3 Value and SPARC Value of Japanese Patients of Dermatological Disease Other than Melanoma (n=22) and Japanese Melanoma Patients (n=56) (FIG. 9)

ELISA measurement of serum GPC3 (FIG. 9 (*a*)) and ELISA measurement of serum SPARC (FIG. 9 (*b*)) of 56 cases of Japanese melanoma patients were performed. In GPC3, 25 cases of 56 cases were positive, and the positive ratio was 44.6%, and in SPARC, 12 cases of 56 cases were positive, and the positive ratio was 21.4%. Comparison between the group of 56 melanoma patients and the group of 22 patients of a dermatological disease other than melanoma was performed using Mann-Whitney U test. The results of test of a GPC3 measured value are shown in FIG. 9 (*a*), and the results of test of SPARC are shown in FIG. 9 (*b*). By the test, $P<0.001$ was obtained in GPC3, and $P=0.009$ was obtained in SPARC, and a significant difference was recognized between two groups.

[3-A-5]

Figure 10:
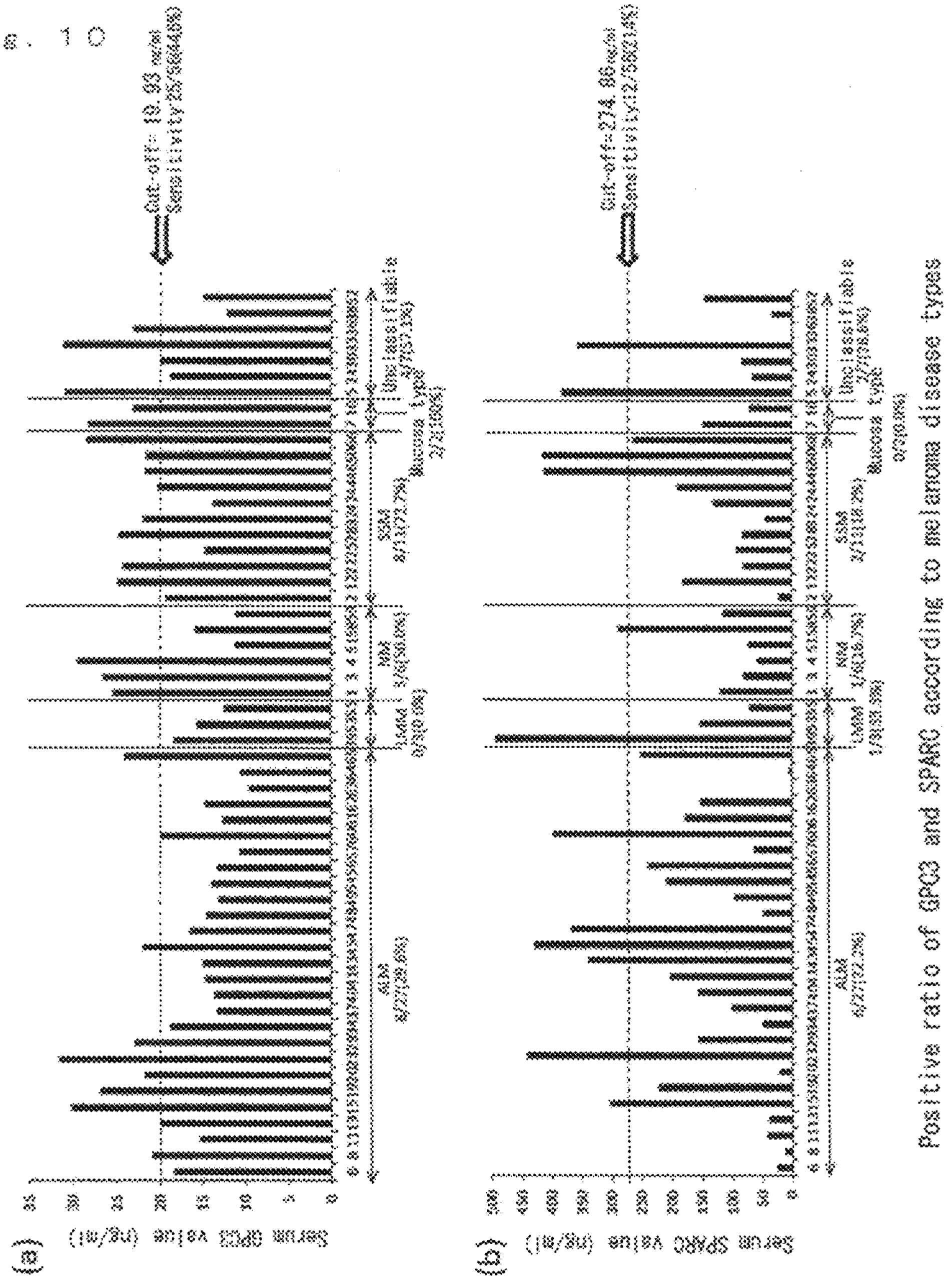
FIG. 10 shows the positive ratio of GPC3 (a) and SPARC (b) according to melanoma disease types.

Positive Ratios of GPC3 and SPARC According to Melanoma Disease Types (FIG. 10)

The positive ratios according to disease types of GPC3 were such that the positive ratio was 29.6% in ALM (8 cases of 27 cases), the positive ratio was 0% in LMM (no detection in 3 cases), the positive ratio was 50% in NM (3 cases of 6 cases), the positive ratio was 72.7% in SSM (8 cases of 11 cases), and the positive ratio was 100% in a mucosa type (2 cases of 2 cases), and the positive ratio was 57.1% in an unclassified case (4 cases of 7 cases) (FIG. 10 (*a*)). The results of ELISA measurement according to disease types of SPARC are shown in FIG. 10 (*b*). The positive ratios according to disease types were such that the positive ratio was 22.2% in ALM (6 cases of 27 cases), the positive ratio was 33.3% in LMM (one case of 3 cases), the positive ratio was 16.7% in NM (one case of 6 cases), the positive ratio was 18.2% in SSM (2 cases of 11 cases), the positive ratio was 0% in a mucosa type (0 case of 2 cases), and the positive ratio was 28.6% in an unclassifiable case (2 cases of 7 cases).

[3-A-6]

Figure 11:
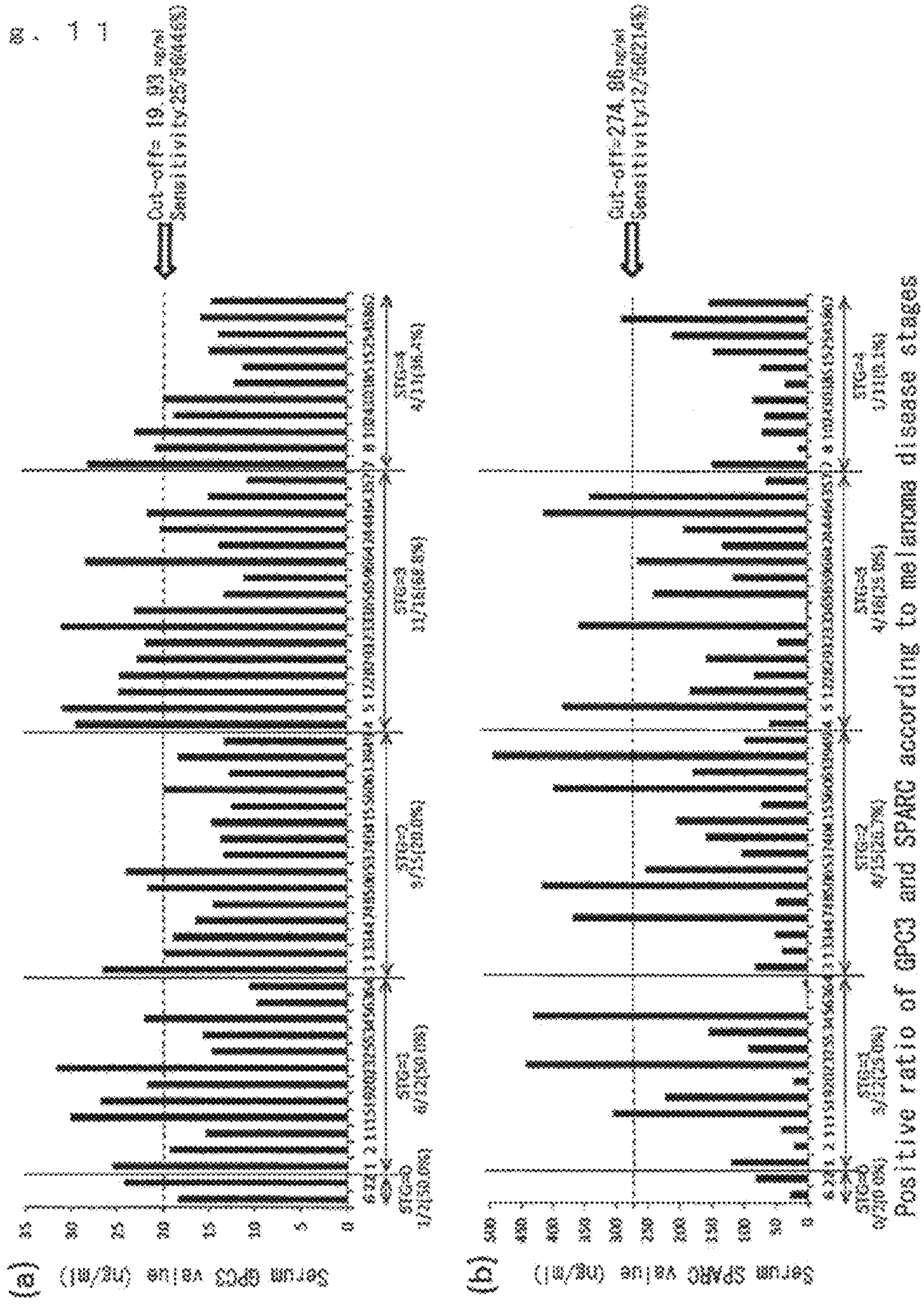
FIG. 11 shows the positive ratio of GPC3 (a) and SPARC (b) according to melanoma disease stages.

Positive Ratios of GPC3 and SPARC According to Melanoma Disease Stages (FIG. 11)

The positive ratios according to disease stages of GPC3 of 56 cases of Japanese patients are shown in FIG. 11 (*a*), and the positive ratios according to disease stages of SPARC of 56 cases of Japanese patients are shown in FIG. 11 (*b*). The positive ratio of GPC3 was 50% at stage 0 (one case of 2 cases), 50% at stage 1 (6 cases of 12 cases), 20% at stage 2 (3 cases of 15 cases), 68.8% at stage 3 (11 cases of 16 cases), and 36.4% at stage 4. The positive ratio of SPARC was 0% at stage 0 (0 case of 2 cases), 25% at stage 1 (3 cases of 12 cases), 26.7% at stage 2 (4 cases of 15 cases), 25% at stage 3 (4 cases of 16 cases), and 9.1% at stage 4 (1 case of 11 cases).

[3-A-7]

Figure 12:
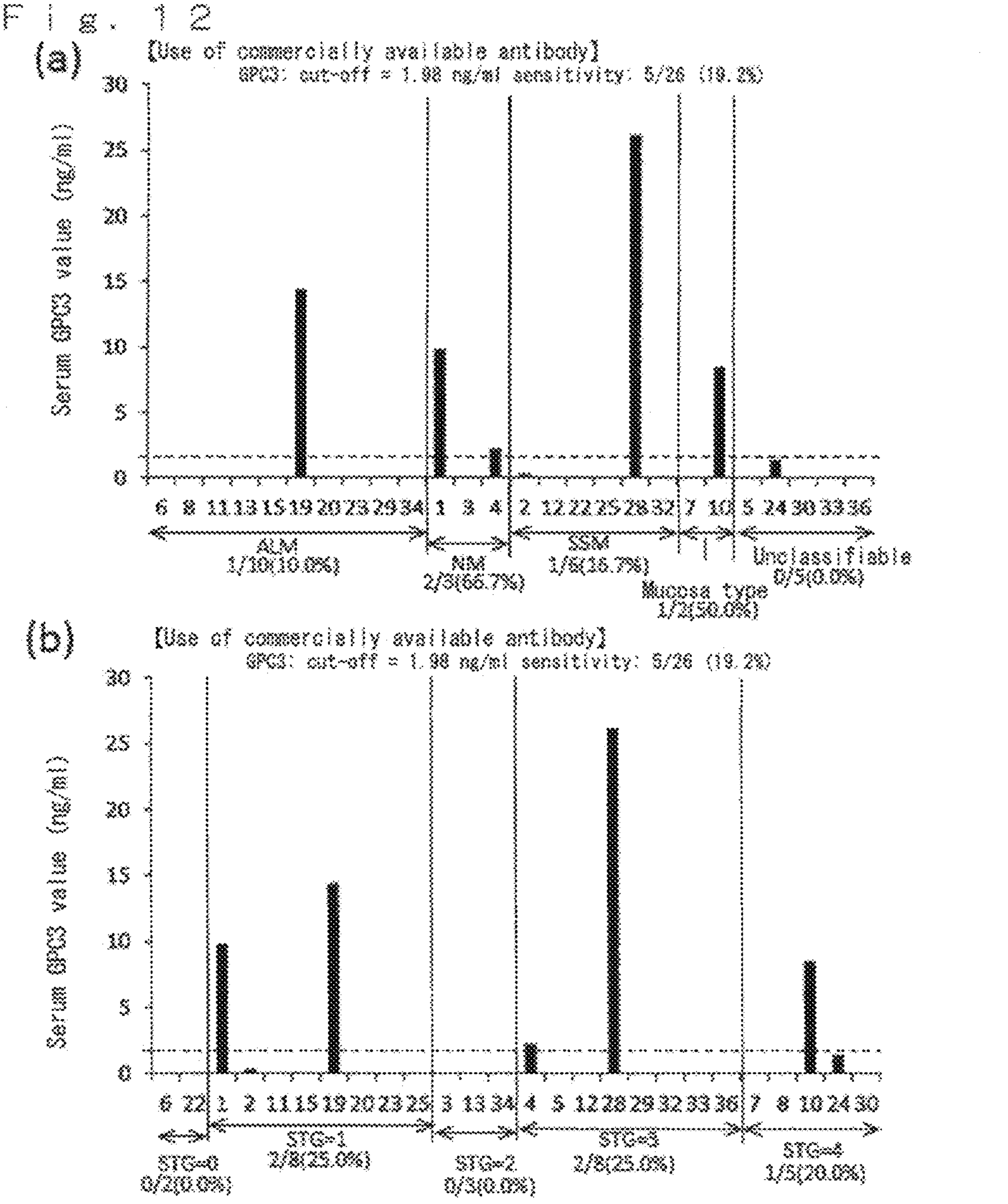
FIG. 12 shows performance of sandwich ELISA using a commercially available antibody for detecting GPC3 (according to disease types (a) and disease stages (b)).

Performance of Sandwich ELISA Using Commercially Available Antibody for Detecting GPC3 (According to Disease Types/Disease Stages) (FIG. 12)

The results of ELISA of GPC3 using a commercially available antibody using specimens of 26 cases before treatment of Japanese melanoma patients are shown in FIG. 12. The results according to disease types are shown in FIG. 12 (*a*), and the results according to disease stages are shown in FIG. 12 (*b*). When cut-off determined from an average value 0.80 ng/mL of 199 cases of healthy subjects of GPC3 (ratio of men to women: 99/100, average age: 62.4 years old), and a standard deviation 1.18 was let to be 1.98 ng/mL (dotted line), the positive ratio was 19.2% (5 cases of 26 cases were positive). When compared with the positive ratio in ELISA using a novel antibody (FIGS. 9 to 11), detection sensitivity was apparently more excellent in the novel antibody.

[3-A-8]

Figure 13:
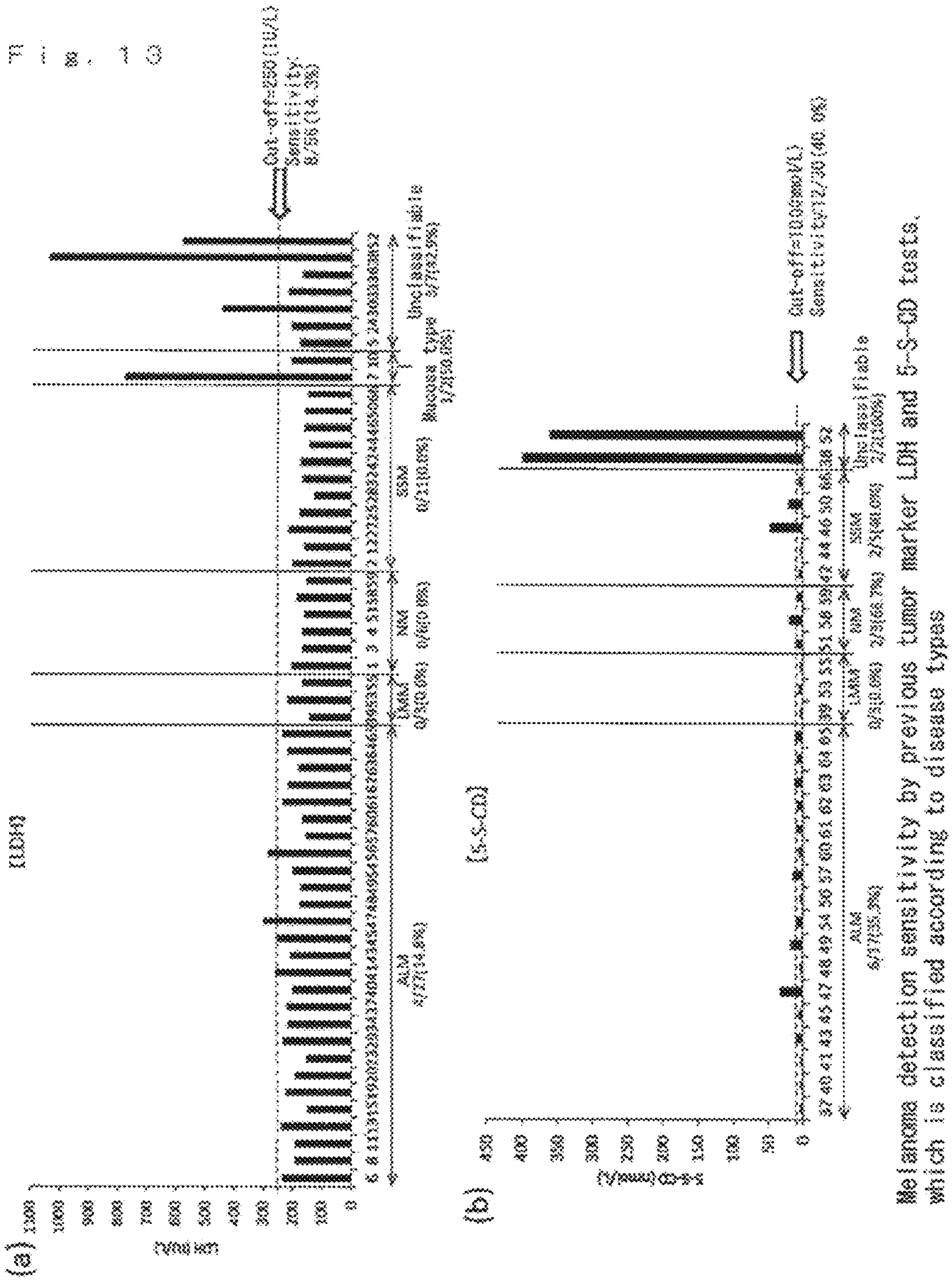
FIG. 13 shows melanoma detection sensitivity with the previous tumor marker LDH (a) and 5-S-CD (b) tests which are classified according to disease types.

Melanoma Detection Sensitivity by Previous Tumor Marker LDH and 5-S-CD Tests, which is Classified According to Disease Types (FIG. 13)

FIG. 13 (*a*) shows the results of LDH measurement of 30 cases of the same serum samples as serum samples which were studied by a novel method, by a disease type. LDH was measured using a JSCC standardization corresponding method, and a case in which the result exceeded a standard value range (110 to 250 IU/L) was determined to be positive. According to disease types (FIG. 13 (*a*)), 4 cases of 27 cases were positive in ALM (14.8%), there was no detection of positive case in LMM, NM and SSM (0%), 3 cases of 7 cases were positive in an unclassifiable case (42.9%), and one case of 2 cases was positive in a mucosa type (50%). Eight cases of all 56 cases were positive, and the total positive ratio was 14.3%.

The results of 5-S-CD measurement of 30 melanoma cases are shown in FIG. 13 (*b*). In measurement of 5-S-CD, a case in which the result exceeded a standard value range (1.5 to 10 nmol/L) using a HPLC method was determined to be positive. Six cases of 17 cases were positive in ALM (35.3%), there was no detection of positive case in LMM, 2 cases of 3 cases were positive in NM (66.7%), 2 cases of 5 cases were positive in SSM (40%), 2 cases of 2 cases were positive in an unclassifiable case (100%), 12 cases of all 30 cases were positive, and the total positive ratio was 40%.

[3-A-9]

Figure 14:
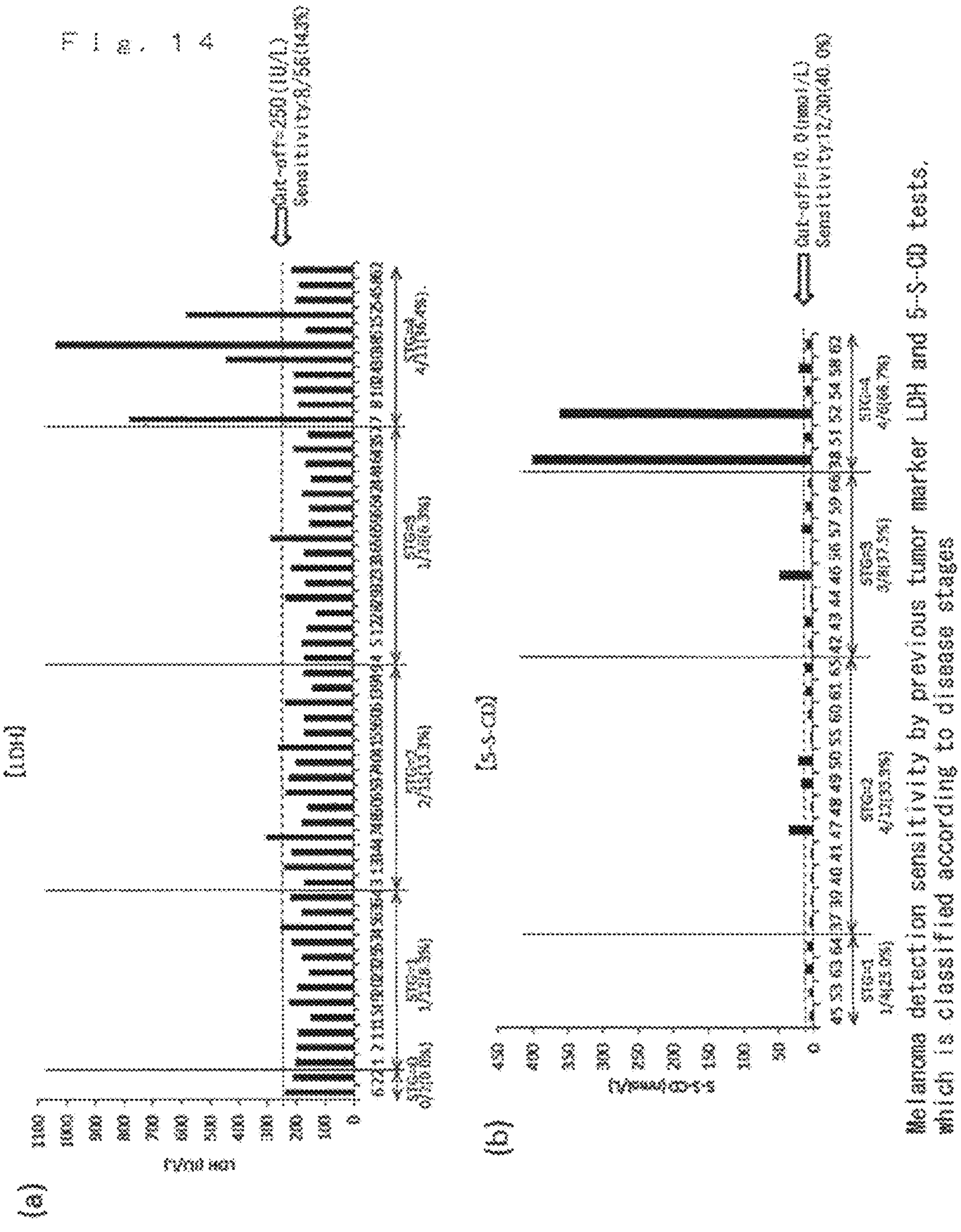
FIG. 14 shows melanoma detection sensitivity with the previous tumor marker LDH (a) and 5-S-CD (b) tests which are classified according to disease stages.

Melanoma Detection Sensitivity by Previous Tumor Marker LDH and 5-S-CD Tests, which is Classified According to Disease Stages (FIG. 14)

The results of LDH measurement of 56 Japanese melanoma patient cases according to disease stages are shown in FIG. 14 (*a*). There was no detection case among 2 cases at stage 0 (0%), one case of 12 cases was positive at stage 1 (8.3%), 2 cases of 15 cases were positive at stage 2 (13.3%), one case of 16 cases was positive at stage 3 (6.3%), and 4 cases of 11 cases were positive at stage 4 (36.4%).

In FIG. 14 (*b*), the results of 5-S-CD measurement of 30 melanoma cases are shown according to disease stages. One case of 4 cases was positive at stage 1 (positive ratio 25%), 4 cases of 12 cases were positive at stage 2 (positive ratio 33.3%), 3 cases of 8 cases were positive at stage 3 (positive ratio 37.5%), and 4 cases of 6 cases were positive at stage 4 (positive ratio 66.7%).

[3-A-10]

Detection Number and Positive Ratio in the Case of GPC3 and SPARC Alone, or when they are Combined, According to Disease Types, and Detection Number of Existing Tumor Marker and Positive Ratio (Table 8)

The results which are summarized according to melanoma disease types are shown. The positive ratio by means of GPC3 of ALM which is a disease type frequent in a Japanese was 29.6% (8 cases of 27 cases were detected), and the positive ratio by means of SPARC was 22.2% (6 cases of 27 cases). The positive ratio by means of a combination of GPC3 and SPARC was 40.7%. Melanoma of the European and American white race is mostly SSM, and SSM was positive at 72.7% by means of GPC3 (8 cases of 11 cases), and 18.2% by means of SPARC (2 cases of 11 cases), and the positive ratio by means of a combination of GPC3 and SPARC was 72.7%. High sensitivity was shown in SSM which accounts for a majority of melanoma of the European and American white race than in ALM which is frequent in Japanese. The result is that in all 56 cases, when the positive ratio of GPC3 (44.6%) and the positive ratio of SPARC (21.4%) were combined, it resulted in that the positive ratio is 53.6% (30 cases of 56 cases), and in a diagnostic method by combining GPC3 and SPARC, diagnostic performance of melanoma is enhanced than in diagnosis with a tumor marker alone.

In LDH measurement in the previous method, 4 cases of 27 cases were positive and the positive ratio was 14.8% in ALM, and 6 cases of 17 cases were positive and the positive ratio was 35.3% in 5-S-CD. LDH could detect no case of SSM among 11 cases. By means of 5-S-CD, 2 cases of 5 cases detected, and the positive ratio was 40% in SSM. By means of LDH, 8 cases of all 56 cases were positive, and the positive ratio was 14.3%, and by means of 5-S-CD, 12 cases of all 30 cases were positive, and the positive ratio was 40%. Diagnosis by a combination of GPC3 and SPARC of the novel method was more excellent than diagnosis with LDH or 5-S-CD in whole melanoma, and also in diagnosis of ALM and SSM.

[3-A-11]

Detection Number and Positive Ratio in the Case of GPC3 and SPARC Alone, or when they are Combined, and Existing Tumor Marker Detection Number and Positive Ratio, According to Disease Stages (Table 9)

The positive ratio by means of a combination of GPC3 and SPARC was 50% at stages 0 to 1. The positive ratio was 40% at stage 2, and the positive ratio was 75% at stage 3. The positive ratio was 45.5% at stage 4. From the foregoing results, it was shown that, regardless of a progressive stage, melanoma can be diagnosed by measurement of GPC3 and SPARC, and further, a case at an early stage which cannot be determined by the previous method such as a LDH test can be diagnosed by the novel method.

When the results of a LDH test and a 5-S-CD test were classified according to disease stages, the previous method using LDH and 5-S-CD exhibited the efficacy in diagnosis at stage 4, but the positive ratio by means of LDH was 8.3% and the positive ratio by means of 5-S-CD was 25% at stage 1, while the positive ratio was 50% by means of a combination of GPC3 and SPARC of the novel method. The novel method is effective in diagnosis at an early stage. At stage 2, the positive ratio was 13.3% by means of LDH and the positive ratio was 33.3% by means of 5-S-CD, while the positive ratio was 40% by the novel method, and at stage 3, the positive ratio was 6.3% by means of LDH, and the positive ratio was 37.5% by means of 5-S-CD, while the positive ratio was 75% by the novel method, and thus, the novel method was more excellent than the existing tumor markers. The result was that diagnosis by means of a combination of GPC3 and SPARC has predominance as compared with the previous method, in respect that melanoma can be diagnosed regardless of a disease stage. Although in diagnosis at stage 4 in which a possibility of cure is low, and there is remote metastasis, the novel method is inferior to 5-S-CD, in diagnosis of melanoma at stages 0 to 3 in which there is no remote metastasis, and there is a possibility of complete cure, the positive ratio by means of LDH was 8.9% and the positive ratio by means of 5-S-CD was 33.3%, while the positive ratio by the novel method was 55.6%, being excellent. Particularly, at stages 0 to 1 in which a possibility of complete cure is as high as almost 100%, the positive ratio by the novel method was 50%, and the excellent diagnosis results were obtained.

TABLE 8

The detection number and the positive ratio in the case of GPC3 and SPARC alone, or when they are combined, and the existing tumor marker detection number and the positive ratio, according to disease types

| Disease type | ALM | LMM | NM | SSM | Mucosa type | Unclassifiable | Whole |
|---|---|---|---|---|---|---|---|
| Novel method_GPC3 detection number (%) | 8/27(29.6) | 0/3(0.0) | 3/6(50.0) | 8/11(72.7) | 2/2(100) | 4/7(57.1) | 25/56(44.6) |
| Commercially available antibody_GPC3 detection number (%) | 1/10(10.0) | — | 2/3(66.7) | 1/6(16.7) | 1/2(50.0) | 0/5(0.0) | 5/26(19.2) |
| Novel method_SPARC detection number (%) | 6/27(22.2) | 1/3(33.3) | 1/6(16.7) | 2/11(18.2) | 0/2(0.0) | 2/7(28.6) | 12/56(21.4) |
| Novel method_GPC3 and SPARC detection number (%) | 11/27(40.7) | 1/3(33.3) | 4/6(66.7) | 8/11(72.7) | 2/2(100) | 4/7(57.1) | 30/56(53.6) |
| Previous method_LDH detection number (%) | 4/27(14.8) | 0/3(0.0) | 0/6(0.0) | 0/11(0.0) | 1/2(50.0) | 3/7(42.9) | 8/56(14.3) |
| Previous method_5-S-CD detection number (%) | 6/17(35.3) | 0/3(0.0) | 2/3(66.7) | 2/5(40.0) | — | 2/2(100) | 12/30(40.0) |

TABLE 9

The detection number and the positive ratio in the case of GPC3 and SPARC alone, or when they are combined, and the existing tumor marker detection number and the positive ratio, according to disease stages

| Disease stage | 0 | 1 | 2 | 3 | 4 | Stages 0 to 3 | Whole stage |
|---|---|---|---|---|---|---|---|
| Novel method_GPC3 detection number (%) | 1/2(50.0) | 6/12(50.0) | 3/15(20.0) | 11/16(68.8) | 4/11(36.4) | 21/45(46.7) | 25/56(44.6) |
| Commercially available antibody_GPC3 detection number (%) | 0/2(0.0) | 2/8(25.0) | 0/3(0.0) | 2/8(25.0) | 1/5(20.0) | 4/21(19.0) | 5/26(19.2) |
| Novel method_SPARC detection number (%) | 0/2(0.0) | 3/12(25.0) | 4/15(26.7) | 4/16(25.0) | 1/11(9.1) | 11/45(24.4) | 12/56(21.4) |
| Novel method_GPC3 and SPARC detection number (%) | 1/2(50.0) | 6/12(50.0) | 6/15(40.0) | 12/16(75.0) | 5/11(45.5) | 25/45(55.6) | 30/56(53.6) |
| Previous method_LDH detection number (%) | 0/2(0.0) | 1/12(8.3) | 2/15(13.3) | 1/16(6.3) | 4/11(36.4) | 4/45(8.9) | 8/56(14.3) |
| Previous method_5-S-CD detection number (%) | 0/0(—) | 1/4(25.0) | 4/12(33.3) | 3/8(37.5) | 4/6(66.7) | 8/24(33.3) | 12/30(40.0) |

[3-B] Results of Study Using Australian Specimen

[3-B-1]

Figure 15:
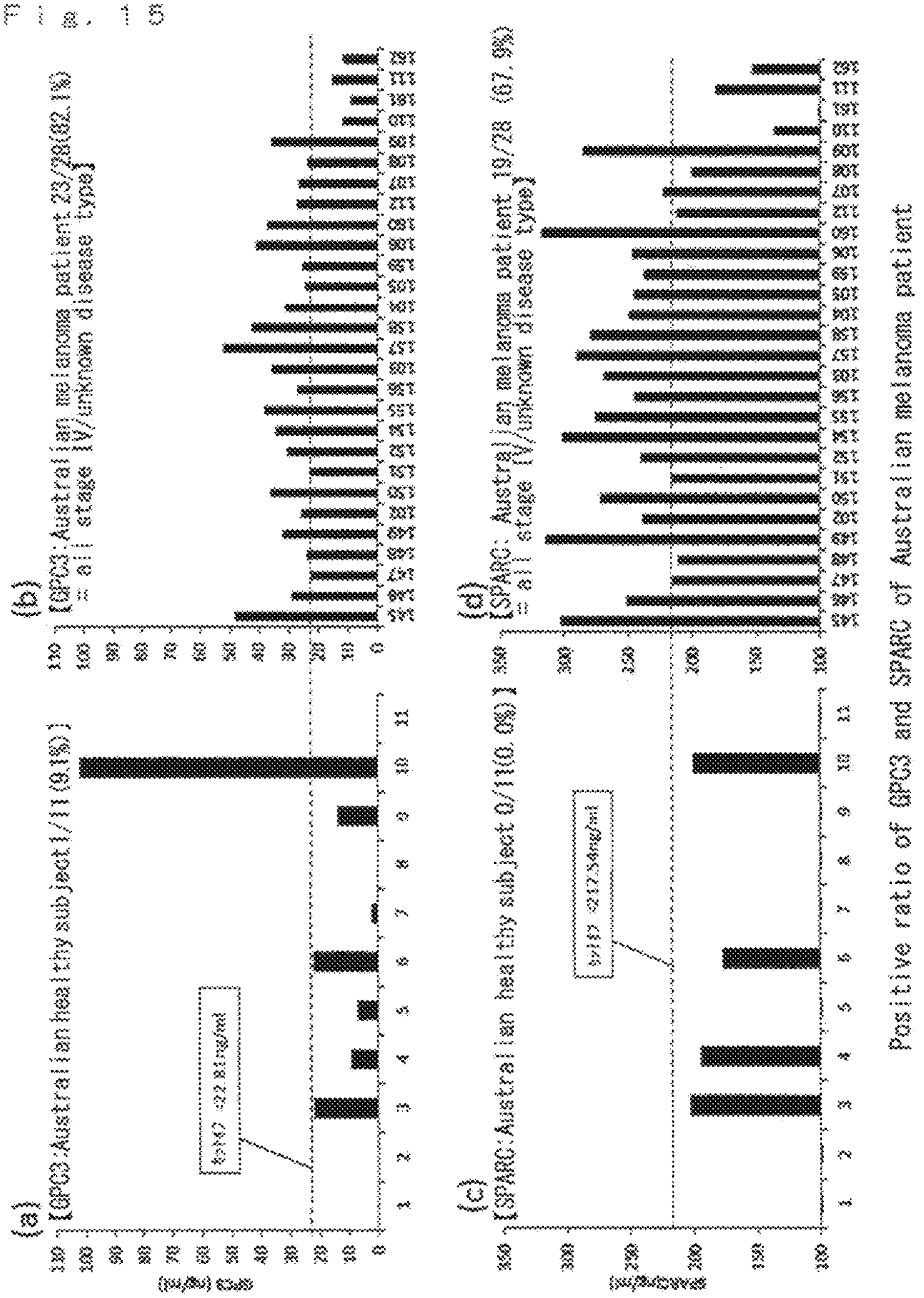
FIG. 15 shows the positive ratio of GPC3 ((a) and (b)) and SPARC ((c) and (d)) of Australian healthy subject (a) and (c) and melanoma patients ((b) and (d)).
Figure 10:
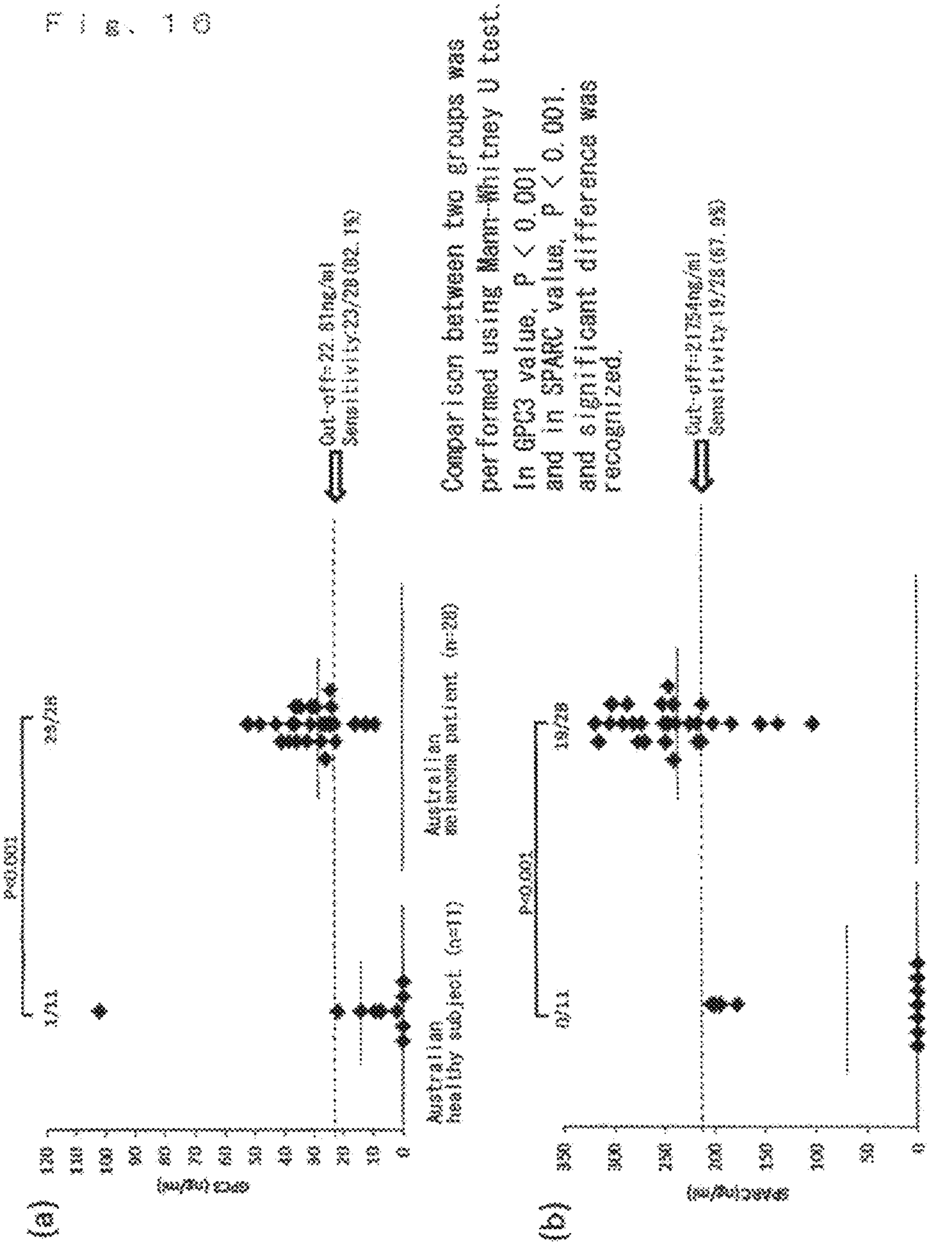

Positive Ratio by Means of GPC3 and SPARC of Australian Melanoma Patient (FIG. 15)

The results of GPC3 detection of 11 Australian melanoma healthy subject cases (FIG. 15 (*a*)) and the results of GPC3 detection of 28 patient cases (FIG. 15 (*b*)) are shown. Concerning the positive ratio of a patient group, the positive ratio of Australian melanoma patients was calculated from a cut-off value determined from Australian healthy subjects (expressed by a dotted line; 22.81 ng/mL). The healthy subject group included one healthy subject case which apparently exhibited a high value. Clinical setting of melanoma patients was such that their disease type was unknown (thought to be mostly SSM), and all patients were at stage 4, and 23 cases of 28 cases were positive, the positive ratio was 82.1%, and thus, detection sensitivity was high.

Also by means of SPARC, similarly, a cut-off value of SPARC (expressed by a dotted line; 217.54 ng/mL) was determined from 11 Australian cases, and the SPARC positive ratio of melanoma patients was calculated (FIG. 15 (*d*)). There was no false positive case in 11 cases of the healthy subject group (FIG. 15 (*c*)). Nineteen cases of 28 cases were positive, and the positive ratio of the melanoma patient group was 67.9%.

[3-B-2]

Distribution of GPC3 Values and SPARC Values of Australian Healthy Subjects (n=11) and Australian Melanoma Patients (n=28) (FIG. 16)

Measured values of a melanoma patient group and a healthy subject group are shown in FIG. 16 as a scatter diagram. In the case of 28 melanoma patients and 11 healthy subjects, when comparison was performed between two groups using Mann-Whitney U test, $P<0.001$ was obtained by means of GPC3, and $P<0.001$ was obtained by means of SPARC, and a significant difference was recognized.

[Accession Number]

TABLE 10

| Clone Name | Domestic Accession Number | Date of Acceptance | Date of Request for Transfer from Domestic Deposition to International Deposition | International Accession Number | Issue Date of International Form of Receipt (Scheduled Accession Number) |
|---|---|---|---|---|---|
| 2C11 | NITE P-1326 | Apr. 23, 2012 | | | |
| 2E11 | NITE P-1327 | Apr. 23, 2012 | | | |
| 2H10 | | Apr. 23, 2012 | Apr. 1, 2013 | NITE BP-01328 | Jun. 7, 2013 |
| 3E3 | NITE P-1329 | Apr. 23, 2012 | Jun. 12, 2013 | | Not yet issued at Int'l Filing Date. (NITE BP-01329) |
| 3E10 | | Apr. 23, 2012 | Apr. 1, 2013 | NITE BP-01330 | Jun. 7, 2013 |
| 3E11 | | Apr. 23, 2012 | Apr. 1, 2013 | NITE BP-01331 | Jun. 7, 2013 |
| 4F5 | NITE P-1332 | Apr. 23, 2012 | | | |
| 5E5 | NITE P-1333 | Apr. 23, 2012 | | | |
| 7C8 | NITE P-1334 | Apr. 23, 2012 | | | |
| 7G6 | NITE P-1335 | Apr. 23, 2012 | | | |
| 10A4 | NITE P-1336 | Apr. 23, 2012 | | | |
| U3E | | Apr. 23, 2012 | Apr. 1, 2013 | NITE BP-01337 | Jun. 7, 2013 |
| S2F9 | | Apr. 23, 2012 | Apr. 1, 2013 | NITE BP-01338 | Jun. 7, 2013 |
| S14A7 | NITE P-1339 | Apr. 23, 2012 | | | |
| S14C12 | NITE P-1340 | Apr. 23, 2012 | | | |
| S19B1 | NITE P-1341 | Apr. 23, 2012 | | | |
| S20D10 | NITE P-1342 | Apr. 23, 2012 | | | |
| S23C10 | | Apr. 23, 2012 | Apr. 1, 2013 | NITE BP-01343 | Jun. 7, 2013 |
| S23E9 | NITE P-1344 | Apr. 23, 2012 | Jun. 12, 2013 | | Not yet issued at Int'l Filing Date. (NITE BP-01344) |
| S25H9 | | Apr. 23, 2012 | Apr. 1, 2013 | NITE BP-01345 | Jun. 7, 2013 |

INDUSTRIAL APPLICABILITY

The kit for diagnosing melanoma and the method of detecting melanoma using a combination of monoclonal antibodies of the present invention is very useful for conducting diagnosis of melanoma, particularly, at an early stage, which is precise and highly specific.

The invention claimed is:

1. A method of detecting malignant melanoma, comprising contacting (1) a composition comprising one or more anti-GPC3 monoclonal antibodies selected from the group consisting of mAb2C11, mAb2E11, mAb2H10, mAb3E3, mAb3E10, mAb3E11, mAb4F5, mAb5E5, mAb7C8, mAb7G6, mAb10A4 and mAbU3E, produced by one or more hybridomas selected from the group consisting of clone names 2C11, 2E11, 2H10, 3E3, 3E10, 3E11, 4F5, 5E5, 7C8, 7G6, 10A4 and U3E, which were deposited at National Institute of Technology and Evaluation (NITE), NITE Patent Microorganisms Depositary (NPMD) on Apr. 23, 2012 under accession numbers NITE P-1326, NITE P-1327, NITE BP-01328, NITE P-1329, NITE BP-01330, NITE BP-01331, NITE P-1332, NITE P-1333, NITE P-1334, NITE P-1335, NITE P-1336 and NITE BP-01337, respectively, and (2) a composition comprising one or more anti-SPARC monoclonal antibodies selected from the group consisting of mAbS2F9, mAbS14A7, mAbS14C12, mAbS19B1, mAbS20D10, mAbS23C10, mAbS23E9 and mAbS25H9, produced by one or more hybridomas selected from the group consisting of clone names S2F9, S14A7, S14C12, S19B1, S20D10, S23C10, S23E9 and S25H9, which were deposited at NPMD on Apr. 23, 2012 under accession numbers NITE BP-01338, NITE P-1339, NITE P-1340, NITE P-1341, NITE P-1342, NITE BP-01343, NITE P-1344 and NITE BP-01345, respectively, with a sample from a subject.

2. The detection method according to claim 1, wherein the sample is blood, serum or plasma of a subject.

3. The detection method according to claim 2, wherein the subject is caucasian.

4. The detection method according to claim 1, which is performed by an ELISA method.

5. The detection method according to claim 1, which is performed by an immunostaining method.

* * * * *